US008101390B2

(12) United States Patent
Takagi

(10) Patent No.: US 8,101,390 B2
(45) Date of Patent: Jan. 24, 2012

(54) MUTANT-TYPE ACETYLTRANSFERASE MPR1

(75) Inventor: Hiroshi Takagi, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 336 days.

(21) Appl. No.: 12/309,271

(22) PCT Filed: Feb. 27, 2007

(86) PCT No.: PCT/JP2007/053667
§ 371 (c)(1),
(2), (4) Date: Mar. 24, 2009

(87) PCT Pub. No.: WO2008/007475
PCT Pub. Date: Jan. 17, 2008

(65) Prior Publication Data
US 2010/0196987 A1    Aug. 5, 2010

(30) Foreign Application Priority Data

Jul. 14, 2006  (JP) ................................. 2006-194365

(51) Int. Cl.
*C12N 9/12* (2006.01)
*C12N 1/00* (2006.01)
*C12N 15/00* (2006.01)
*C07H 21/04* (2006.01)

(52) U.S. Cl. .................. 435/193; 435/254.1; 435/320.1; 536/23.2

(58) Field of Classification Search .................. 435/193, 435/254.1, 320.1; 536/23.2
See application file for complete search history.

(56) References Cited

U.S. PATENT DOCUMENTS

2010/0196987 A1*  8/2010  Takagi .......................... 435/193

FOREIGN PATENT DOCUMENTS

JP         9-234058       9/1997
JP         2006-067806    3/2006

OTHER PUBLICATIONS

H. Takagi et al., "*Saccharomyces cerevisiae* Σ1278b Has Novel Genes of the N-Aceytltransferase Gene Superfamily Required for L-Proline Analogue Resistance," J. Bacteriol., vol. 182, No. 15, pp. 4249-4256, 2000.

M. Shichiri et al., "A Novel Acetyltransferase Found in *Saccharomyces cerevisiae* Σ1278b That Detoxifies a Proline Analogue, Azetidine-2-carboxylic Acid," J. Bio. Chem., vol. 276, No. 45, pp. 41998-42002, Nov. 9, 2001.

C. Hoshikawa et al., "A nonconserved Ala401 in the yeast RspS ubiquitin ligase is involved in degradation of Gap1 permease and stress-induced abnormal proteins," Proc. Natl. Acad. Sci., vol. 100, No. 20, pp. 11505-11510, 2003.

Y. Kimura et al., "Polymorphism of the MPR1 gene required for toxic proline analogue resistance in the *Saccharomyces cerevisiae* complex species," Yeast, vol. 19, pp. 1437-1445, 2002.

M. Nomura et al., "Characteristization of Novel Acetyltransferases Found in Budding and Fission Yeasts That Detoxify a Proline Analogue, Azetidine-2-Carboxylic Acid," J. Biochem., vol. 133, pp. 67-74, 2003.

M. Nomura et al., "Role the yeast acetyltransferase Mpr1 in oxidative stress: Regulation of oxygen reactive species caused by a toxic proline catabolism intermediate," Proc. Natl. Acad. Sci., vol. 101, No. 34, pp. 12616-12621, 2004.

W. Li et al., "Proline Biosynthesis in *Saccharomyces cerevisiae*: Molecular Analysis of the *PRO1* Gene, Which Encodes γ-Glutamyl Kinase," J. Bacteriol., vol. 174, No. 12, pp. 4148-4156, 1992.

Y. Terao et al., "Gene Dosage Effect of L-Proline Biosynthetic Enzymes on L-Proline Accumulation and Freeze Tolerance in *Saccharomyces cerevisiae*," Applied and Environmental Microbiology, vol. 69, No. 11, pp. 6527-6532, 2003.

H. Takagi et al., "Kobo ni Hakken shita 'Acetyl-ka Koso Mprl' ni yoru Atarashii Ko Sanka," vol. 44, No. 2, pp. 83-84, Feb. 2006.

K. Iitani et al., "Random Hen'I Donyu ni yoru Kobo Acetyltransferase Mprl no Sanka Stress Taisei Kojo," Japan Society for Bioscience, Biotechnology and Agrochemistry Kansai Shibu Koenkai Koen Yoshishu, vol. 2006, p. 32(C13), Sep. 2006.

K. Iitani et al., "Random Hen'I Donyu ni yoru Kobo Acetyltransferase Mprl no Sanka Stress Taisei Kojo," Japan Society for Bioscience, Biotechnology and Agrochemistry Kansai Shibu Koenkai Koen Yoshishu, vol. 2006, p. 32(C13), Sep. 2006. [with English translation].

* cited by examiner

*Primary Examiner* — Tekchand Saidha
(74) *Attorney, Agent, or Firm* — Wenderoth, Lind & Ponack, L.L.P.

(57) ABSTRACT

The present invention provides a mutant-type acetyltransferase Mpr1: which comprises an amino acid sequence of a yeast wild-type Mpr1 represented by SEQ ID NO:1, wherein at least one amino acid at positions 63 to 65 and 117 of the amino acid sequence is substituted and said mutant-type acetyltransferase Mpr1 exhibits a higher antioxidant capacity than the wild-type Mpr1. The mutant-type acetyltransferase Mpr1 of the present invention exhibits a higher resistance to oxidative stress compared to the wild-type Mpr1. The present invention further provides a gene encoding the mutant-type Mpr1, a vector comprising the gene and a yeast transformed with the gene.

8 Claims, 20 Drawing Sheets dent # MUTANT-TYPE ACETYLTRANSFERASE MPR1

This application is a U.S. national stage of International Application No. PCT/JP2007/053667 filed Feb. 27, 2007.

TECHNICAL FIELD

The present invention relates to a mutant-type acetyltransferase Mpr1 which exhibits an improved resistance to oxidative stress.

BACKGROUND ART

A novel gene MPR1 which was previously found in a yeast *Saccharomyces cerevisiae* S1278b strain by the present inventor (non-patent literature 1) codes for N-acetyltransferase (Mpr1) which detoxifies the toxic analogue of amino acid proline, azetidine-2-calboxylate (AZC), by the acetylation of AZC (FIG. 1) (non-patent literature 2).

AZC enters into cells via proline permease and is incorporated into proteins by competing with proline upon protein synthesis. As a result of the incorporation of AZC, proteins with abnormal structures and impaired functions accumulate in cells and inhibit the cell growth. In cells which express MPR1, AZC is subjected to the N-acetylation in cytosol and is not incorporated into nascent proteins and therefore, such cells are thought to acquire AZC resistance (non-patent literature 3).

As a result of homology search, homologous genes which have similar functions as MPR1 from fission yeast *Schizosaccharomyces pombe* and, sibling species of *S. cerevisiae*, *S. paradoxus* (ppr1$^+$, Spa MPR1) were identified (non-patent literatures 4 and 5) and therefore, MPR1 is believed to be widely distributed among yeasts. However, interestingly, *S. cerevisiae* S288C strain which was used for the genomic analysis of yeasts and sake yeast lack MPR1. MPR1 is located near the subtelomeric region of 14th chromosome of S1278b strain. A homologous gene (MPR2) which differs from MPR1 only at the 85th residue is located near the subtelomeric region of 10th chromosome and there is no difference in the functions between MPR1 and MPR2 (non-patent literature 1). Comparing S288C strain and S1278b strain, though some genes show base substitutions and deletions, no gene other than MPR1 that is present only in S1278b strain and codes for a certain phenotype has been reported.

AZC is rare in nature and therefore, is probably not the intrinsic substrate of MPR1 product (Mpr1). Accordingly, the present inventors analyzed the biological function of Mpr1 and identified the intracellular substrate of the same (non-patent literature 6). Firstly, cells of MPR1•MPR2 disruptant were exposed to oxidative stresses such as hydrogen peroxide and heat shock. As a result, the MPR1•MPR2 disruptant showed decreased survival rate and increased intracellular reactive oxygen species (ROS) level compared to the wild-type strain. On the other hand, when multicopies of MPR1 were introduced into *S. cerevisiae* 288C strain which originally lacks MPR1 and MPR2, the strain exhibited increased survival rate under oxidative stress and decreased ROS level. Accordingly, it was confirmed that Mpr1 lowers the intracellular oxidative level. PUT2 disruptant which accumulates a metabolic intermediate of proline, $\Delta^1$-pyrroline-5-calboxylate (P5C), was confirmed to show growth impairment and increase in ROS level. Therefore, the role of Mpr1 in PUT2 disruptant was examined thereafter. The result showed that when MPR1 and MPR2 in PUT2 disruptant are disrupted, the growth is strongly inhibited and the ROS level is increased, whereas the overexpression of MPR1 decreased the ROS level. Further, the analysis using a recombinant enzyme showed that Mpr1 acetylates P5C or glutamate-gamma-semialdehyde (GSA) which is in equilibrium to P5C. From the above results, it is suggested that the intracellular accumulation of P5C leads to the generation of ROS which causes the cytotoxicity and that Mpr1 regulates the ROS level via the acetylation of P5C/GSA so as to alleviate the oxidative stress (FIG. 2) (non-patent literature 6).

Under the fermentative production environment, yeasts are subjected to various stresses such as cold temperature, freezing, drying, oxidation, high osmolarity, high ethanol concentration and biased nutrition. Long term exposure of yeast to such stresses as above brings about the cleavage of noncovalent bondings in the intracellular proteins which leads to exposure of hydrophobic amino acids on the surfaces of the proteins and generation of "abnormal proteins" which lost their normal structures and functions, and results in the restriction of the useful functions of the yeast. In particular, the oxidative stress is generated by various factors such as heat shock, hydrogen peroxide, freezing (freezing-thawing) damage, high ethanol concentration and the like and is a great cause of the inhibition of the growth of the yeast cells. In the fields of fermented food products and brewed food products, there is a desire for breeding a yeast which is highly resistant to the oxidative stress.

So far, the present inventors found that an amino acid proline has a property of protecting yeasts from stresses such as freezing, drying, oxidation and the like (Patent literature 1). Further, the present inventors found that a yeast strain whose gene encoding proline degradative enzyme was disrupted by the genetic engineering acquires the ethanol resistance by accumulating proline in the cells (Patent literature 2).

Patent literature 1: JP-A-9-234058
Patent literature 2: JP-A-2006-67806
Non-patent literature 1: H. Takagi et al., J. Bacteriol., 182, 4249-4256 (2000)
Non-patent literature 2: M. Shichiri et al., J. Biol. Chem., 276, 41998-42002 (2001)
Non-patent literature 3: C. Hoshikawa et al., Proc. Natl. Acad. Sci. U.S.A., 100, 11505-11510 (2003)
Non-patent literature 4: Y. Kimura et al., Yeast, 19, 1437-1445 (2002)
Non-patent literature 5: M. Nomura et al., J. Biochem., 133, 67-74 (2003)
Non-patent literature 6: M. Nomura et al., Proc. Natl. Acad. Sci. U.S.A., 101, 12616-12621 (2004)

DISCLOSURE OF INVENTION

Problem to be Solved by the Invention

An object of the present invention is to provide a mutant-type acetyltransferase Mpr1 with an increased antioxidant capacity by modifying Mpr1. A further object of the present invention is to provide a yeast with an increased antioxidant capacity by transforming the yeast with a gene encoding the mutant-type Mpr1.

Means for Solving the Problem

The present invention provides a mutant-type acetyltransferase Mpr1, which comprises: an amino acid sequence of a wild-type yeast Mpr1 represented by SEQ ID NO:1, wherein at least one amino acid at positions 63 to 65 and 117 of the amino acid sequence is substituted and said mutant-type acetyltransferase Mpr1 exhibits a higher antioxidant capacity than the wild-type Mpr1.

In the present invention, the phrase "exhibits a higher antioxidant capacity than the wild-type Mpr1" means that the yeast transformed with a gene encoding the mutant-type Mpr1 shows increased resistance to one or more of the stresses selected from the group consisting of AZC stress, heat shock stress, hydrogen peroxide stress, freezing stress and ethanol stress compared to the yeast having the wild-type Mpr1. The resistances to these stresses can be confirmed by the stress sensitivity tests which are described in Examples.

The present invention further provides a gene encoding the mutant-type acetyltransferase Mpr1, a vector comprising the gene and a yeast transformed with the gene.

Effect of the Invention

The mutant-type acetyltransferase Mpr1 of the present invention exhibits an increased antioxidant capacity compared to the wild-type enzyme. In other words, the mutant-type Mpr1 of the present invention shows an increased resistance to the oxidative stress which is caused by various stimuli such as freezing-thawing, high concentration of ethanol and the like. Therefore, the introduction of the mutant-type acetyltransferase Mpr1 of the present invention into yeasts which are employed in the fermented food industry and the like provides a yeast exhibiting high resistances to freezing stress, ethanol stress or the like. Such improved yeasts of the invention are applicable, for example, to the development of freezed bread dough which can be stored for long time and to the production of various types of alcoholic beverage with good efficiency.

BEST MODE FOR CARRYING OUT THE INVENTION

Figure 1:
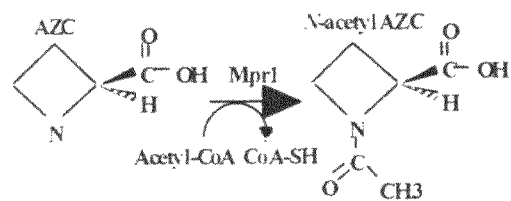
FIG. 1 shows the mechanism of the acetylation of azetidine-2-calboxylate (AZC) by Mpr1.
Figure 2:
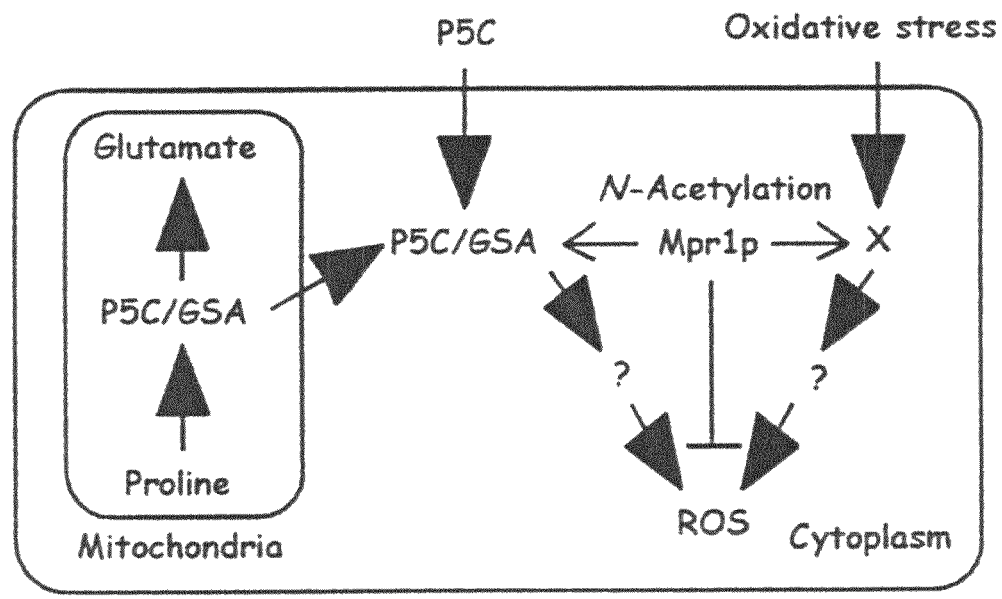
FIG. 2 shows a schematic diagram of the mechanism of regulating the intracellular reactive oxygen species (ROS) level by Mpr1 under the oxidative stress.

The mutant-type Mpr1 of the present invention comprises an amino acid sequence having at least one amino acid substitution at positions 63 to 65 and 117 of the amino acid sequence represented by SEQ ID NO:1 and exhibits a higher antioxidant capacity than the wild-type Mpr1 which comprises the amino acid sequence represented by SEQ ID NO:1.

Examples of especially preferable mutant-type Mpr1s of the present invention include Mpr1s having following substitutions in the amino acid sequence represented by SEQ ID NO:1; a substitution of lysine at position 63 with arginine (K63R, SEQ ID NO:7), a substitution of phenylalanine at position 65 with leucine (F65L, SEQ ID NO:8), a substitution of leucine at position 117 with valine (L117V, SEQ ID NO:9) and substitutions of phenylalanine at position 65 and leucine at position 117 with leucine and valine respectively (F65L/L117V, SEQ ID NO:10).

The present invention also provides genes encoding the above-described amino acid sequences. Examples of the gene of the present invention include, but are not limited to, a gene having at least one modified codon corresponding to positions 63 to 65 and 117 of the wild-type MPR1 whose DNA sequence is represented by SEQ ID NO: 2, wherein the at least one modified codon codes for the amino acid of the corresponding substituted position in the mutant-type Mpr1. Mutant-type Mpr1s amino acid sequences are represented by SEQ ID NOS: 7 to 10.

The present invention further provides a transformed yeast which is produced by introducing the gene of the present invention to the yeast and which exhibits an increased antioxidant capacity.

The yeast to which the gene of the present invention is introduced is not limited and any type of yeasts can be used.

The yeast may or may not have an endogenous MPR1 or MPR1 homologue with the same function as MPR1.

Examples of yeasts include those which are used in the production of fermented or brewed food such as sake yeast, alcohol yeast, wine yeast, baker's yeast and the like. Preferable yeasts are those belonging to *Saccharomyces* and more preferable yeasts are those belonging to *Saccharomyces cerevisiae*.

The yeasts to be transformed by the method of the present invention include those which are modified to exhibit other advantageous properties by means of genetic engineering or the like. Examples of the modified yeasts which exhibit the advantageous properties include the yeast whose gene encoding proline degradative enzyme is disrupted as described in JP-A-2006-67806 to the present inventors. The yeast accumulates proline in the cell and therefore, exhibits a high ethanol resistance.

The method for introducing the gene into a yeast is not limited and any conventional method may be employed depending on the yeast to be transformed. The method for introducing a gene into a yeast can be found for example in textbooks such as "Bio-manual series 10, Experimental procedures for gene analysis using yeast" (YODOSHA CO., LTD.) and "Experimental procedures of biological chemistry 39, Molecular genetic experimental procedures using yeast" (Japan Scientific Societies Press).

In particular, an expression vector for a yeast can be created by preparing an open reading frame (ORF) of a gene of interest by known methods such as PCR and ligating the ORF downstream to a promoter which directs the gene expression in the yeast to give a gene cassette. The present invention also provides a vector comprising a gene encoding the mutant-type Mpr1 of the present invention.

The vector of the present invention can be constructed by adding appropriate restriction sites at both ends of the gene prepared for example by PCR, digesting the gene with the restriction enzymes and ligating, by using DNA ligase, the gene into a plasmid vector which had been digested with appropriate restriction enzymes. The DNA which is introduced into a plasmid can be readily amplified, isolated and purified by the use of *E. coli*.

The yeast promoter may be any promoter which is known to be used for the expression in yeast and examples of the yeast promoter include GAL1, GAL10, PHO5, PGK1, ADH1, AOX1 and the like. Especially preferable yeast promoters are GAL1 and ADH1.

The vector of the present invention preferably includes a replication origin such as that derived from 2 µm DNA and a selection marker such as LEU2, URA3, TRP1 and the like. Further, if necessary, the vector of the present invention may include enhancer, terminator, ribosomal binding site, polyadenylation signal sequence and the like. Many types of vectors used for yeasts are commercially available and one may select a vector depending on the type of the yeast to be used as a host.

When the yeast has the endogenous MPR1 gene or homologue thereof, the endogenous MPR1 gene or homolog gene thereof may be replaced with the mutant-type MPR1 gene of the present invention or the endogenous MPR1 gene and the mutant-type MPR1 gene of the present invention may exist together in the yeast cell.

When the endogenous MPR1 or homolog thereof and the mutant-type MPR1 gene of the present invention exist together in the yeast cell or when the yeast does not have the endogenous MPR1 or homolog thereof, the transformation of the mutant-type MPR1 gene may be carried out by using an autonomous replicating plasmid vector. Examples of the autonomous replicating plasmid vector include those having the replication origin derived from 2 µm plasmid such as pAD4 (LEU2 marker), pYES2 (URA3 marker) which were used in Examples and the like.

When the endogenous MPR1 presented on the yeast chromosome is replaced with the gene encoding the mutant-type Mpr1 of the present invention, one may use a plasmid vector which includes a selection marker gene for yeast but does not include an autonomous replicating sequence. By using such vectors, the sequence of MPR1 or homolog thereof on the chromosome and the sequence on the plasmid undergo the homologous recombination and then the transformant in which the plasmid is inserted into the chromosome DNA can be obtained. Such plasmid vectors are commercially available and include pRS405 (LEU2 marker) (Stratagene), pRS406 (URA3 marker) and the like. When such a plasmid vector is used, one portion of the interior of MPR1 carried by the plasmid should be digested with a unique restriction enzyme to make a linearized plasmid which is then used for the transformation.

The present invention also provides a mutant-type acetyltransferase which has at least one amino acid substitution at positions corresponding to positions 63-65 and 117 of the wild-type acetyltransferase Mpr1 sequence and exhibits a higher antioxidant capacity compared to the wild-type acetyltransferase. The present invention further provides a gene encoding the mutant-type acetyltransferase, a vector comprising the gene and a yeast transformed with the gene encoding the mutant-type acetyltransferase.

Especially preferable examples are the mutant-type acetyltransferase which has arginine at the position corresponding to position 63 of the wild-type acetyltransferase Mpr1, the mutant-type acetyltransferase which has leucine at the position corresponding to position 65 of the wild-type acetyltransferase Mpr1 and the mutant-type acetyltransferase which has valine at the position corresponding to position 117 of the wild-type acetyltransferase Mpr1.

Examples of a wild-type acetyltransferase include, but are not limited to, enzymes which belong to the acetyltransferase superfamily, such as enzymes (SEQ ID NOS: 3 and 5) encoded by MPR1 homolog genes (Spa MPR1, ppr1$^+$) (SEQ ID NOS: 4 and 6) which exist in *S. paradoxus* and *Schizosaccharomyces pombe*.

EXAMPLES

The present inventors prepared the mutant-type MPR1 genes by introducing random mutations into the wild-type MPR1 gene and introduced the mutant-type MPR1 genes into Mpr1 non-carrying yeasts. The present inventors screened the clones, from the transformed yeasts, which exhibit higher resistances to heat shock stress, AZC stress and hydrogen peroxide stress compared to the wild-type strain and obtained the acetyltransferase Mpr1 of the present invention with improved functions.

Materials and Methods

1) Materials i) Strains

<Budding Yeast, *Saccharomyces cerevisiae*>

S288C strain

CKY8 (MATa ura3-52 leu2-3,112)

CKY263 (MATa ura3-52 leu2-3,112 GAL) (gifted from Chris A. Kaiser (Massachusetts Institute of Technology))

<*E. coli* (*Escherichia coli*)>

JM109:

recA1 end1 gyrA96 thi1 hsdR17 sup E44 relA1 Δ(lac-proAB)/F'[traD36 proAB+lacIg lacZ ΔM15] (purchased from TAKARA BIO INC.)

DH5a:
F-λ-f80lac Z ΔM15 Δ (lacZYA-argF) U169 deoR recA1 endA1 hsdR17 (rK− mK+) supE44 thi-1 gyrA96 (purchased from TAKARA BIO INC.)
(ii) Plasmids
pAD4 (gifted from Dr. Junichi Nigawa, Kyushu Institute of Technology)

Plasmid pAD4 includes a replication origin derived from 2 μmDNA, a selection marker for yeast, LEU2, a replication origin for *E. coli* and a selection marker, ampicillin resistance gene. pAD4 also includes ADH1 promoter upstream of a multicloning site and ADH1 terminator downstream of the multicloning site.

pYES2 (Purchased from Invitrogen)

Plasmid pYES2 includes a replication origin derived from 2 μmDNA, a selection marker for yeast URA3, a replication origin for *E. coli* and a selection marker, ampicillin resistance gene. pYES2 also includes a multicloning site downstream of GAL1 promoter and a transcription termination signal derived from CYC1 gene.

pMH1 (Constructed by The Present Inventor)

pMH1 is a plasmid constructed by introducing Sau3AI fragment (about 5.4 kb) comprising MPR1 genomic DNA into BamHI site of pYES2. MPR1 genomic DNA was obtained by digesting FHS06 genomic DNA with Sau3AI. As described in non-patent literature 1, FHS06 is an AZC resistant mutant.

pAD-MPR (Constructed by the Present Inventor)

paD-MPR is a plasmid constructed by introducing HindIII-SacI fragment (about 700 bp) comprising MPR1 ORF into HindIII-SacI site of pAD4. In pAD-MPR, the expression of MPR1 is driven by ADH1 promoter in the presence of glucose.

pGAL-MPR (Constructed by the Present Inventor)

HindIII-MluI fragment (about 930 bp) containing MPR1 ORF was excised from MPR1 genomic DNA and the fragment was introduced into HindIII-MluI site of pYES2 to give a plasmid pGAL-MPR. In pGAL-MPR, the expression of MPR1 is driven by GAL1 promoter in the presence of galactose.

2) Media
YPD Medium (Complete Medium for Yeast)

TABLE 1

| Glucose | 2% |
|---|---|
| Bacto peptone | 2% |
| Bacto yeast extract | 1% |

SD Medium (Minimal Medium for Yeast: the Nitrogen Source is $(NH_4)_2SO_4$)

TABLE 2

| Glucose | 2% |
|---|---|
| Bacto yeast nitrogen base without amino acids (Difco) | 0.67% |

SG Medium (Minimal Medium for Yeast: the Nitrogen Source is $(NH_4)_2SO_4$ and the Carbon Source is Galactose)

TABLE 3

| Galactose | 2% |
|---|---|
| Bacto yeast nitrogen base without amino acids (Difco) | 0.67% |

SC Medium (Complete Synthesis Medium for Yeast; SC Medium is Prepared by Adding Some Necessary Components for the Synthesis to SD Medium)

TABLE 4

| Glucose | 2% |
|---|---|
| Bacto yeast nitrogen base without amino acids (Difco) | 0.67% |
| *Drop-out mixture | 0.2% |

*Drop-out mixture is the mixture obtained by combining the amino acids listed below. Depending on the purpose, a certain amino acid is removed and the remaining amino acids are well mixed to give Drop-out mixture.

TABLE 5

| L-aspartic acid | 0.5 g | L-alanine | 2.0 g |
|---|---|---|---|
| L-glutamine | 2.0 g | L-asparagine | 2.0 g |
| Glycine | 2.0 g | L-cysteine HCL | 2.0 g |
| Inositol | 2.0 g | L-glutamic acid | 2.0 g |
| L-leucine | 2.0 g | L-histidine | 2.0 g |
| L-methionine | 2.0 g | L-isoleucine | 2.0 g |
| L-phenylalanine | 10.0 g | L-lysine | 2.0 g |
| L-serine | 2.0 g | p-aminobenzoic acid | 0.2 g |
| L-tryptophan | 2.0 g | L-proline | 2.0 g |
| Uracil | 2.0 g | L-threonine | 2.0 g |
| L-aspartic acid | 2.0 g | L-tyrosine | 2.0 g |
| L-glutamine | 2.0 g | L-valine | 2.0 g |

When needed, agar (2%) and/or energy source (uracil, leucine and the like) were added to the above-described media. Culture of yeasts was carried out at a temperature of 30° C. When yeasts were cultured in liquid media, they were cultured in a test tube with aluminium cap or a shake flask with silicone plug.

LB Medium (Complete Medium for *E. coli*)

TABLE 6

| Tryptone | 1% |
|---|---|
| Bacto yeast extract | 1% |
| NaCl | 0.5% |

When needed, ampicillin (Amp) (50 μg/ml) and agar (2%) were added to LB medium.

3) DNA Oligomer

The synthesis of DNA oligomers used in the present invention was consigned to Hokkaido System Science Co., Ltd and Operon Biotechnologies, Inc. The names and sequences of the oligomers are listed below.

```
143 (+) -9 20mer
                                    (SEQ ID NO: 15)
5'-GCT CGA GAA GCT TCG AAT GC-3'

143 (-) -4 22mer
                                    (SEQ ID NO: 16)
5'-CGA CGC GTC GTT ATT CGT TCT T-3'

F65L (+) 45mer
                                    (SEQ ID NO: 17)
5'-attaactatcttttaaattgcttaatttggaaattgaaagtgg
c-3'

F65L (-) 45mer
                                    (SEQ ID NO: 18)
5'-gccactttcaatttccaaattaagcaatttaaaaagatagttaa
t-3'
```

-continued

L117V (+) 45mer
(SEQ ID NO: 19)
5'-attaactatcttttaaattgcttaatttggaaattgaaagtgg
c-3'

L117V (-) 39mer
(SEQ ID NO: 20)
5'-cttgatgtagaatgtgcccaggagaactgaattccagtc-3' pYES2 (++) 20mer
(SEQ ID NO: 21)
5'-GTT ACA TGC GTA CAC GCG TC-3' pYES2 (-) 21mer
(SEQ ID NO: 22)
5'-GGA TCG GAC TAC TAG CAG CTG-3' pAD4 (++) 20mer
(SEQ ID NO: 23)
5'-TCG TCA TTG TTC TCG TTC CC-3' pAD4 (-) 21mer
(SEQ ID NO: 24)
5'-GTT TTA AAA CCT AAG AGT CAC-3'

HindIII-MPR (+) 26mer
(SEQ ID NO: 25)
5'-GGC CAA GCT TAG ATG GAT GCG GAA TC-3'

SacI-MPR (-) 30mer
(SEQ ID NO: 26)
5'-CCC CGA GCT CTG TCT ATG ATT ATT CCA TGG-3'

4) Stress Sensitivity Test

Each strain was cultured in liquid medium at 30° C. until it reached the logarithmic growth phase. The resulting culture was serially diluted to $10^0$-$10^4$ fold dilution. Each 2 μl was spotted onto SD or SG agar medium and the medium was cultured under each stress condition.

(i) AZC Stress

2 μl of the culture was spotted onto SD or SG agar medium with AZC concentration adjusted to 0.5-1 mg/ml and cultured at 30° C.

(ii) Heat Shock Stress

2 μl of the culture was spotted onto SD or SG agar medium and the medium was subjected to heat shock at 50° C. for 1-2 hours and thereafter, cultured at 30° C.

(iii) Hydrogen Peroxide Stress

2 μl of the culture was spotted onto SD or SG agar medium with hydrogen peroxide concentration adjusted to 1-2 mM and cultured at 20° C.

(iv) Ethanol Stress

2 μl of the culture was spotted onto SD or SG agar medium with ethanol concentration adjusted to 5-10% and cultured at 20° C.

5) Construction of MPR1 Random Mutation Library by Error-Prone PCR

Error-prone PCR was carried out in the following PCR reaction in order to amplify MPR1 gene fragments. The PCR reaction kit was purchased from Promega.

TABLE 7

| Template (10 ng/μl) | 1 μl |
|---|---|
| Taq DNA polymerase (5 U/μl) | 0.25 μl |
| 10 × Reaction buffer | 5 μl |
| MgCl$_2$ (25 mM) | 3 μl |
| *dNTP mix | 4 μl |

TABLE 7-continued

| Primer 143 (+) –9 (10 pM) | 5 μl |
|---|---|
| 143 (−) –4 (10 pM) | 5 μl |
| Sterile water | 26.75 μl |
| | 50 μl |

*dNTP mix dNTP mix was prepared by mixing dATP, dGTP dCTP and dTTP wherein the concentration of one of dATP, dGTP, dCTP and dTTP was lowered to ⅓ or ⅕ compared to the other three. When the concentration of dATP or dTTP was lowered, the concentration was adjusted to ⅓ of the others and when the concentration of dCTP or dGTP was lowered, the concentration was adjusted to ⅕ of the others.

For example, when the concentration of dATP was lowered to ⅕, the following mixture was used.

TABLE 8

| dATP (1.6 mM) | 1 μl |
|---|---|
| dTTP (8.0 mM) | 1 μl |
| dCTP (8.0 mM) | 1 μl |
| dGTP (8.0 mM) | 1 μl |
| dNTP | 4 μl |

Figure 3:
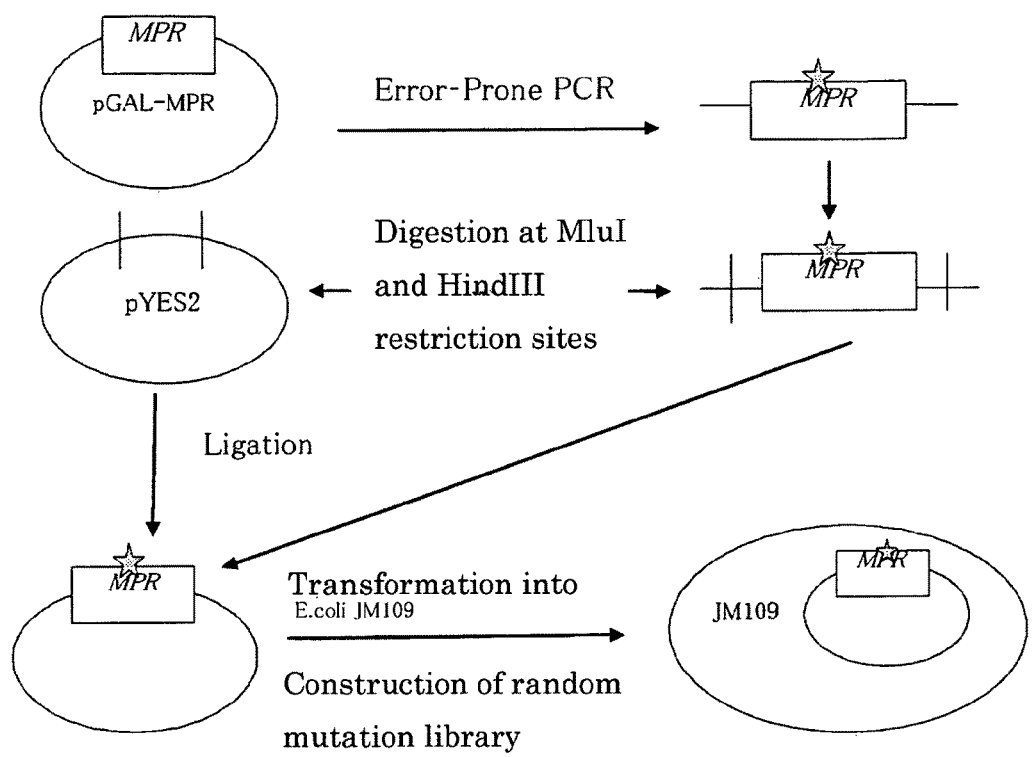
FIG. 3 shows a schematic diagram of the method for constructing MPR1 random mutation library.
Figure 4A:
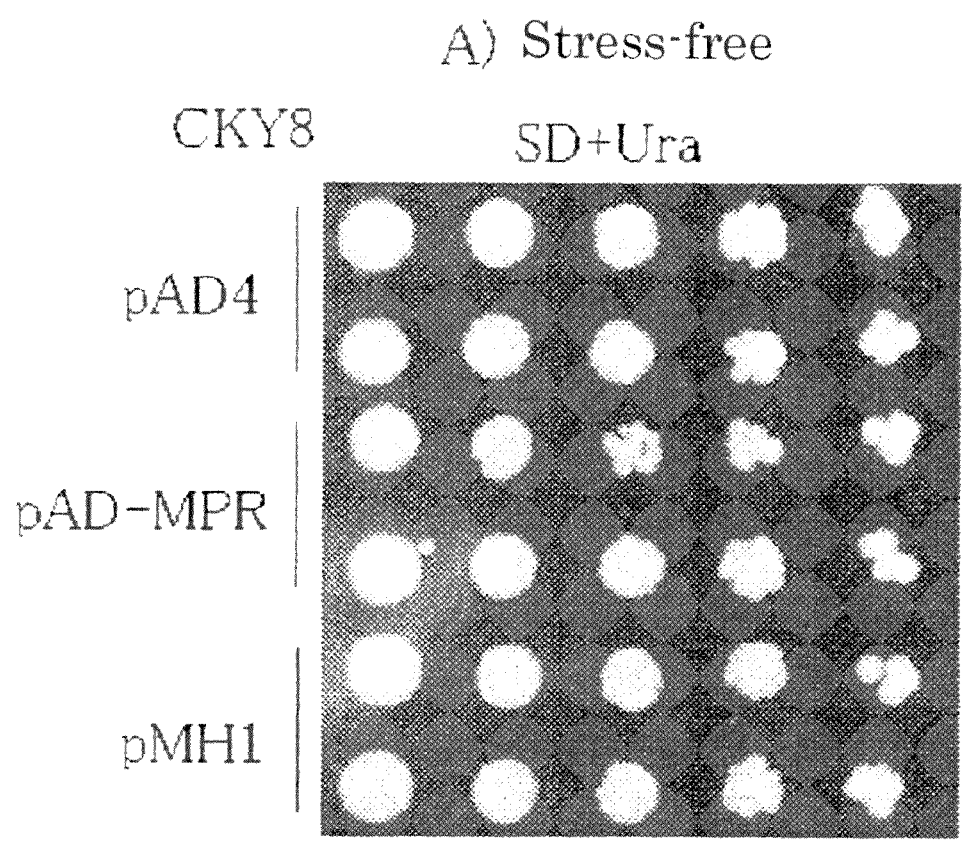
FIG. 4A shows growth of the MPR1 non-carrying strain and the wild-type MPR1-introduced strain under the stress-free condition.
Figure 4B:
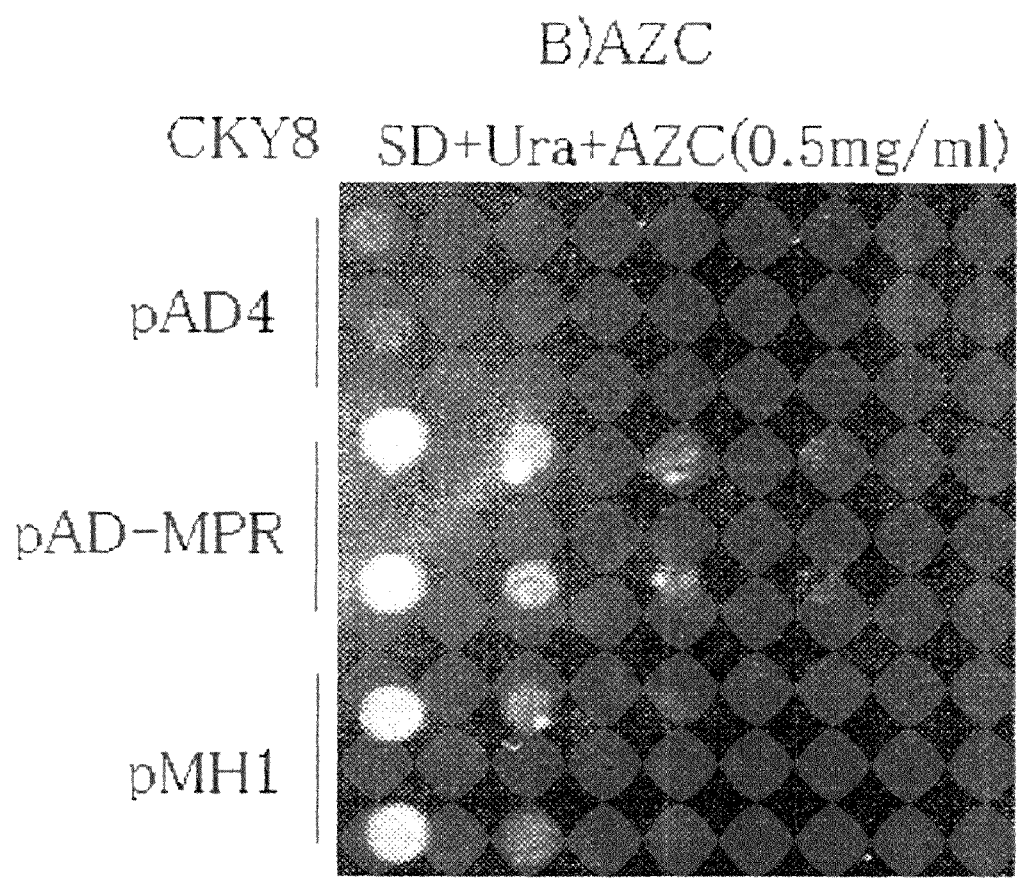
FIG. 4B shows the growth of each strain under the AZC stress condition.
Figure 4C:
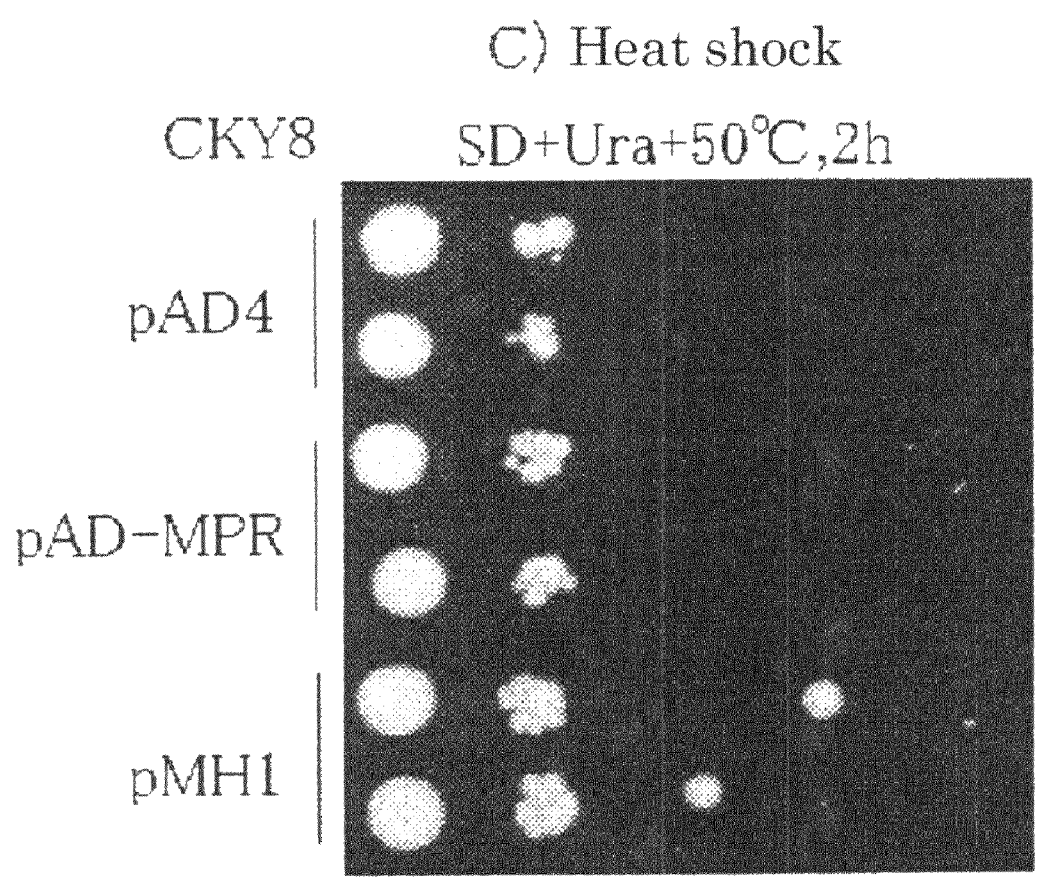
FIG. 4C shows the growth of each strain after the heat shock stress.
Figure 4D:
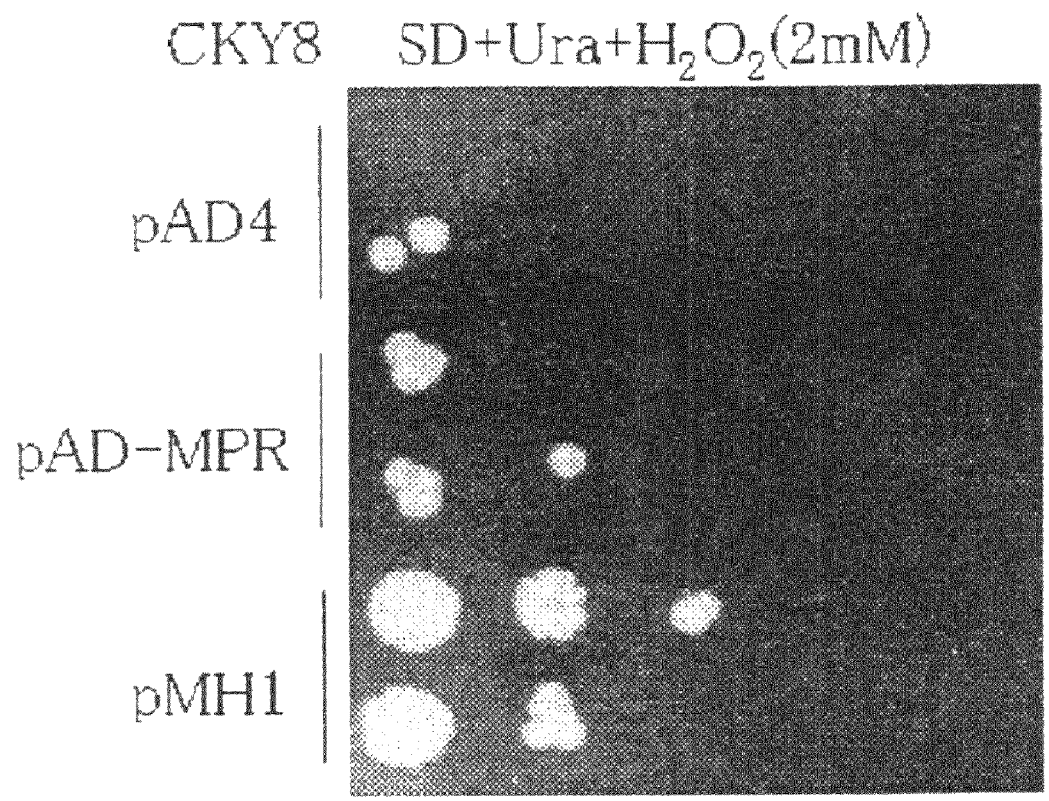
FIG. 4D shows the growth of each strain under the hydrogen peroxide shock.

MPR1 gene fragments (about 930 bp) to which random mutations were introduced with Error-prone PCR were obtained by digesting PCR products with endogenous HindIII and MluI sites, subjecting the digested products to agarose gel electrophoresis and extracting the fragments from the gel. The extraction of DNA fragments from the agarose gel was carried out by using QIAEX II Agarose Gel Extraction kit (QIAGEN). Thus obtained mutant-type MPR1 gene fragments were introduced into HindIII-MluI site of pYES2 and plasmids were prepared from about 60,000 transformed colonies to create a MPR1 random mutation library (FIG. 3). Then the MPR1 random mutation library was introduced into *Saccharomyces cerevisiae* S288C strain.

6) Creation of the Mutant-Type MPR1 Gene-Carrying Strain Which Carries F65L Mutation or L117V Mutation The mutant-type MPR1 genes F65L and L117V were prepared by site-directed mutagenesis using PCR which used pAD4-MPR as a template.

PCR reaction was carried out by using Quik Change® SL Site-Directed Mutagenesis Kit in the following reaction mixture and under the following conditions.

(Reaction Mixture)

TABLE 9

| 10× Reaction buffer | 5 μl |
|---|---|
| pAD-MPR (10 ng/μl) | 1 μl |
| Primer Fw (F65L (+) or L117V (+)) | about 120 μg |
| Primer Rv (F65L (−) or L117V (−)) | about 120 μg |
| dNTP mix | 1 μl |
| Quik Solution | 3 μl |

The reaction mixture was adjusted to total of 50 μl by addition of dH$_2$O and 1 μl of pfuTurbo DNA polymerase (2.5 U/μl) was added to the reaction mixture to carry out PCR reaction.

PCR Reaction Conditions:

$$95° C., 1\ min \rightarrow [95° C., 50\ sec \rightarrow 60° C., 50\ sec \rightarrow 62° C., 9\ min] \times 18\ cycles \rightarrow 68° C., 7\ min \rightarrow 4° C., \infty$$

PCR amplification product was subjected to agarose gel electrophoresis. A band of 690 bp portion was excised and purified using QIAquik gel extraction kit (QIAGEN).

The purified DNA fragment was digested with HindIII and SacI restriction enzymes and the fragment was ligated into the multicloning site of pAD4 vector which had been digested with the same restriction enzymes.

Thus obtained mutant-type MPR1 gene fragment was introduced into HindIII-MluI site of pAD4 and the resulting plasmid was introduced into *Saccharomyces cerevisiae* S288C strain.

7) Measurement of the Survival Rate of the Cells after the Hydrogen Peroxide Treatment Each strain was inoculated into 2 ml of SC-Leu medium and SD medium and was shake-cultured at 30° C. until reaching the logarithmic growth phase. The cells were collected by centrifuging at 3,500 rpm for 5 min. The cells were suspended in 4 ml of 100 mM potassium phosphate buffer (pH7.4) such that the $OD_{600}$ of the suspension was 1.0. To the suspension, hydrogen peroxide was added such that the final concentration of hydrogen peroxide was 3 mM or 6 mM. The obtained cell suspension was shaken at 30° C. 1 ml of the cell suspension without treated by hydrogen peroxide (0 hour) and those treated by hydrogen peroxide for two hours and for four hours were transferred to microtubes. The cell suspensions were serially diluted and applied onto YPD agar medium. Thereafter, the cells were cultured at 30° C. and colonies formed were counted. The survival rate of each sample to the cells without treated by hydrogen peroxide (0 hour) was calculated by taking the colony number formed from the cells of 0 hour treatment as 100%.

8) Measurement of the Intracellular ROS Level after the Hydrogen Peroxide Treatment In order to determine the intracellular reactive oxygen species (ROS) level, 2',7'-dichlorodihydrofluorescein diacetate ($H_2DCFDA$) (Molecular Probes, Inc.) was used as an intracellular oxidation sensitive probe. $H_2DCFDA$ is enzymatically deacetylated by intracellular esterase to give DCFH, which is then oxidized by ROS to give a highly fluorescent substance DCF. The fluorescence intensity of DCF was measured by fluorescence spectrophotometer.

The cells were cultured in 50 ml of SC-Leu medium and SD medium until they reached the logarithmic growth phase and the cells were washed by centrifugation with sterile water and were suspended in 100 mM potassium phosphate buffer (pH7.4) such that $OD_{600}$ of the suspension was 1.0. To 40 ml of this suspension, 5 mM $H_2DCFDA$ was added to the final concentration of 0.01 mM and the suspension was incubated at 30° C. for 15 min. Thereafter, 300 mM hydrogen peroxide was added to the suspension to the final concentration of 3 mM or 6 mM and the suspension was shaken at 30° C. The cells without treated by hydrogen peroxide (0 min) and those treated by hydrogen peroxide for 30 min and 60 min were collected by centrifugation (8,000 rpm, 10 min). The collected cells were washed with sterile water and were suspended in 500 μl of sterile water. To the cell suspension, glass-beads (0.5 mM) were added and cells were lysed by using Multi-beads shocker (MB601U, Yasui Kikai Corporation) (1 min on, 1 min off, five cycles, 0° C.). After centrifugation (15,000 rpm, 10 min), the supernatants were collected. The mixture of 50 μl of the supernatant and 450 μl of sterile water was irradiated with excitation wavelength of 504 nm and the intensity of the emitted fluorescent wavelength (524 nm) was measured by using fluorescence spectrophotometer (Hitachi, Ltd., F4500).

The protein concentration in the supernatant of the cell lysate was measured using a protein quantitative reagent (Bio-Rad). Intracellular ROS level was expressed as fluorescence intensity per protein (mg) which was calculated according to the following formula.

$$SFI = \frac{\text{fluorescence } [EX = 504\ nm/EM = 524\ nm]}{\text{protein (mg/ml)} \times 0.05\ (ml)} \quad \text{[Formula 1]}$$

The result is shown as relative fluorescence intensity based on the fluorescence intensity at 0 min which is taken as 100%.

9) Purification of Mpr1 Enzyme

JM109 was inoculated in 5 ml of M9CA (CA:0.2%) medium and was cultured at. 37° C. until OD600 of the culture reached 0.7. IPTG was added to the medium to the final concentration of 0.1 mM and cells were further cultured at 18° C. for 18 hours. After the culture, cells were ice-cooled and were collected by centrifugation (8000 rpm, 5 min). Cells were washed by the addition of Lysis buffer. After centrifugation (8000 rpm, 5 min), 5 ml of Lysis buffer was added and cells were suspended therein. The suspension was subjected to ultrasonic disintegrator and was centrifuged (15000 rpm, 10 min). The supernatant was applied onto Ni-NTA column (2 ml of QIAGEN resin suspension) equilibrated with Lysis buffer. The flow-through fraction was collected and the column was washed with 10 ml of wash buffer and then fractions were collected. Further, fractions eluted with 5 ml of elution buffer were used as the purified enzyme.

10) Measurement of Enzymatic Activities

Enzymatic activities were measured for the purified wild-type Mpr1 and the purified K63R, F65L/L117V, F65L and L117V-mutant-type Mpr1s. The enzymatic activities were measured according to 5,5'-dithiobis (2-nitrobenzoic acid) (DTNB) method. This method utilizes the fact that Mpr1s enzymatic reaction using acetyl-CoA and AZC as substrates produces CoA, which reacts with SH group to give TNB which exhibits high absorption of light at 412 nm.

The change in absorbance (ABS) at 412 nm per minute at 30° C. was measured using the reaction mixture comprising 1 mM DTNB solution, Mpr1 (about 0.6-0.2 μg/ml) and 0.025 mM-0.15 mM acetyl-CoA or 0.5 mM-5 mM AZC. ΔABS/min (reaction rate) for each concentration of the substrate was measured and the graph ([S]/v-[S] plot) of Michaelis-Menten conversion equation (equation 1) was created to find out Km and Vmax.

$$[S]/v=1/v[S]+Km/V \quad \text{(equation 1)}$$

11) Measurement of Enzyme Stability

The temperature-stabilities of the wild-type Mpr1 and the mutant-type Mpr1s, K63R, F65L/L117V, F65L and L117V were analyzed as follows. The purified enzyme was incubated at 45° C. in water bath and a portion of the enzyme was taken every five minutes and the portion was subjected to ΔABS measurement by DTNB method. The remaining activity (%) of the enzyme preparation at each time point was calculated based on that the absorbance at 412 nm of the enzyme preparation at the beginning of the incubation (0 min) was 100%. A graph was created in which the horizontal axis indicates treatment time and the longitudinal axis indicates remaining activity (%). The stabilities of the wild-type enzyme and the mutant-type enzymes were compared. Further, hydrogen peroxide stabilities were analyzed. The hydrogen peroxide treatment was carried out at the concentration of 0.5M and the enzyme preparation was incubated at 25° C. in water bath and the remaining activities were calculated by the same way as the thermal stability measurement.

12) Introduction of Mpr1 into Proline-Accumulating Yeast

The present inventors previously showed that the substitution of Asp154 with Asn of the amino acid sequence of proline synthetase represented by SEQ ID NO:28 (PRO1:gamma glutamine kinase, Li W., and Brandriss C M., J. Bacteriol., 174, 4148-4156, 1992, NCBI accession #M85293) brought about the proline accumulation in yeast cells JP A 2006-67806). The present inventors further introduced the mutant-type Mpr1 of the present invention into the proline-accumulating yeast and investigated the antioxidant capacity of the yeast.

INVDput1 (the strain derived from invSc1 yeast (purchased from Invitrogen) in which PUT1 gene is replaced with HIS3 gene. Terao Y., et al., Applied and Environmental Microbiology, 2003, Vol. 69, No. 11, pp 6527-6532) was transformed with pUV2 vector (pUV-D154Nprol) and pTV3 vector (pTV-PRO2) to give a transformant (InvDput1 (pUV-D154Nprol) (pTV-PRO2) which is hereinafter called as "proline-accumulating yeast"). The pUV2 vector (pUV-D154Nprol) carried the gene encoding a mutant-type PRO1 wherein aspartic acid (D) at position 154 of the wild-type gamma glutamate kinase is replaced with asparagine (N) and pTV3 vector (pTV-PRO2) carried the wild-type PRO2 gene. The selection of proline-accumulating yeasts was carried out on the selection medium which comprised SD medium and leucine.

According to the same method as the above described section 6), pAD4 vector to which the wild-type Mpr1 or one of the mutant-type Mpr1s was introduced was prepared (pAD-Mpr1 (WT), pAD-MPR1-K63R, pAD-Mpr1-F65L or pAD-Mpr1-L117V). The proline-accumulating yeast was transformed with each of these vectors and the corresponding proline-accumulating-Mpr1-introduced strain was obtained. The transformed yeast was selected on SD medium without leucine.

13) Measurement of the Intracellular Proline Content of the Proline-Accumulating-Mpr1-Introduced Strain The proline content in the proline-accumulating-Mpr1-introduced strain can be measured according to a known method. In particular, the proline content can be obtained as a ratio of proline to dry weight of yeast culture medium.

The dry weight of yeast was determined by measuring absorbance at 600 nm ($OD_{600}$) of the 5 ml SD culture medium in which the yeast had been cultured at 30° C. for 60 hours. The dry weight of yeast was calculated based on the following equation (2):

$$\text{Dry weight (g) per 5 ml culture medium} = OD_{600} \text{ value}/978.45 \quad \text{equation (2)}$$

The proline content was measured by using an amino acid analyzer (JEOL Ltd, AminoTac). Firstly, each yeast strain was cultured in 5 ml SD medium at 30° C. for 60 hours and then subjected to centrifugation at 4,000 rpm for minutes to collect the cells. The cells were washed twice with physiological saline and were suspended in 0.5 ml sterile water. The suspension was subjected to the hot water treatment at 100° C. for 10 minutes and to the centrifugation at 12,000 rpm for 5 minutes. 100 μl of the supernatant was diluted 2-5 fold with 0.02N HCl and the diluted supernatant was subjected to filter sterilization and to the measurement by the amino acid analyzer. 1 ml solution containing a standard amino acid mixture (containing 2.5 μmol/ml of each amino acid) was filter sterilized and was used as an authentic sample.

In the measurement of the survival rate and the ROS level of the proline-accumulating-Mpr-introduced strain, the proline content was calculated as described above and the higher proline accumulation compared to the wild-type yeast was confirmed. The proline content in the wild-type yeast was in average about 0.014% based on the dry weight of the yeast, whereas the proline accumulations in the proline-accumulating yeast and the proline-accumulating-Mpr-introduced strain was about 40 to 60 times higher than the wild-type yeast.

14) Measurement of the ROS Level in Proline-Accumulating-Mpr1-Introduced Strain after the Hydrogen Peroxide Treatment According to the same method as those described in the above section 8), the ROS level after the hydrogen peroxide treatment was measured.

15) Measurement of the Survival Rate of Proline-Accumulating-Mpr1-Introduced Strain after the Hydrogen Peroxide Treatment According to the method described above, each proline-accumulating-Mpr1-introduced strain was treated with hydrogen peroxide of final concentration 6 mM and the survival rate of the strain was measured.

16) Measurement of the Stress Resistances of Proline-Accumulating-Mpr1-Introduced Strain According to the method described above, each proline-accumulating-Mpr1-introduced strain was serially diluted and was spotted on SG+Leu medium or SD medium and the survival rates under AZC stress and ethanol stress were determined.

17) Others

The plasmid preparation from *E. coli* was carried out based on alkaline SDS method using QIAprep Spin Miniprep Kit (QIAGEN). Other genetic engineering procedures such as transformation of *E. coli*, digestion of DNA with restriction enzyme and ligation of DNA were carried out according to "Biomanual series I: Basic techniques in genetic engineering" (YODOSHA CO., LTD.) and "Bio experiments illustrated" (Shujunsha Co. Ltd.). The genetic engineerings employing yeasts were carried out according to "Bio-manual series 10, Experimental procedures for gene analysis using yeast" (YODOSHA CO., LTD.) and "Experimental procedures of biological chemistry 39, Molecular genetic experimental procedures using yeast" (Japan Scientific Societies Press).

Results

1) Confirmation of the Stress Resistance of Mpr1

Mpr1 is reported to detoxify AZC by its acetylation and to protect yeasts from oxidative stresses by decreasing the level of intracellular reactive oxygen species (ROS) which is generated by the heat shock and hydrogen peroxide treatment. Firstly, in order to confirm that Mpr1-introduced strain has an improved stress resistance and an improved AZC resistance compared to Mpr1-non-carrying strain, the stress sensitivity test was carried out. MPR1•MPR2-non-carrying *S. cerevisiae* S288C strain (CKY8) was transformed with pAD4 (vector), pAD-MPR (the plasmid which contains only ORF of MPR1 as an insert and the ORF is expressed under the control of ADH1 promoter) or pMH1 (the plasmid which contains 5.4 kb Sau3AI fragment comprising ORF of MPR1 and the ORF is expressed under the control of MPR1 promoter). Thereafter, the stress sensitivity test based on the spot formation was carried out. The result is shown in FIG. 4. MPR1-introduced strains (pAD-MPR and pMH1) exhibited improved resistances to AZC, heat shock of 50° C. and hydrogen peroxide (2 mM) stresses compared to the MPR1. MPR2 non-carrying strain (pAD4).

2) Screening of Mpr1 with Improved Functions

In order to obtain the Mpr1-introduced strain with improved functions, a screening was carried out. The screening was performed for the transformed CKY263 to which MPR1 random mutation library was introduced (the mutant-type MPR1 multicopy-introduced strains). CKY263 transformed with pYES2 (MPR1•MPR2 non-carrying strain) was used as a negative control and CKY263 transformed with pGAL-MPR (MPR1 multicopy-introduced strain) was used as a control.

i) AZC Stress

Strains to be tested were cultured in SG+Leu medium containing AZC at a concentration of 0.5 mg/ml. MPR1•MPR2 non-carrying strain which is a negative control as well as the wild-type MPR1 multicopy-introduced strain showed significant delays in growth. From the random mutation-introduced strains, the clones whose growths were more rapid than that of the wild-type MPR1 multicopy-introduced strain were selected. As a result, 29 AZC resistance clones were obtained from about 91,000 transformants. From the clones obtained, the mutation sites of the introduced mutant-type MPR1 genes were sequenced. As a result, three types of the mutant-type Mpr1 (K63R, G142S and Q179R) were obtained.

ii) Hydrogen Peroxide Stimulus Resistance

Strains to be tested were cultured in SG+Leu medium containing hydrogen peroxide at a concentration of 3 mM. In this condition, not only MPR1 •MPR2 non-carrying strain which is a negative control but also the wild-type MPR1 multicopy-introduced strain could not form any colony. The transformants to which MPR1 random mutation library was introduced were cultured under the same condition. From about 66,500 transformants, five clones which exhibited an improved hydrogen peroxide resistance were obtained. From the sequencing of the five clones, four types of the mutant-type Mpr1 (K63R, F65L/L117V, I184M and E224V) were identified.

Figure 5:
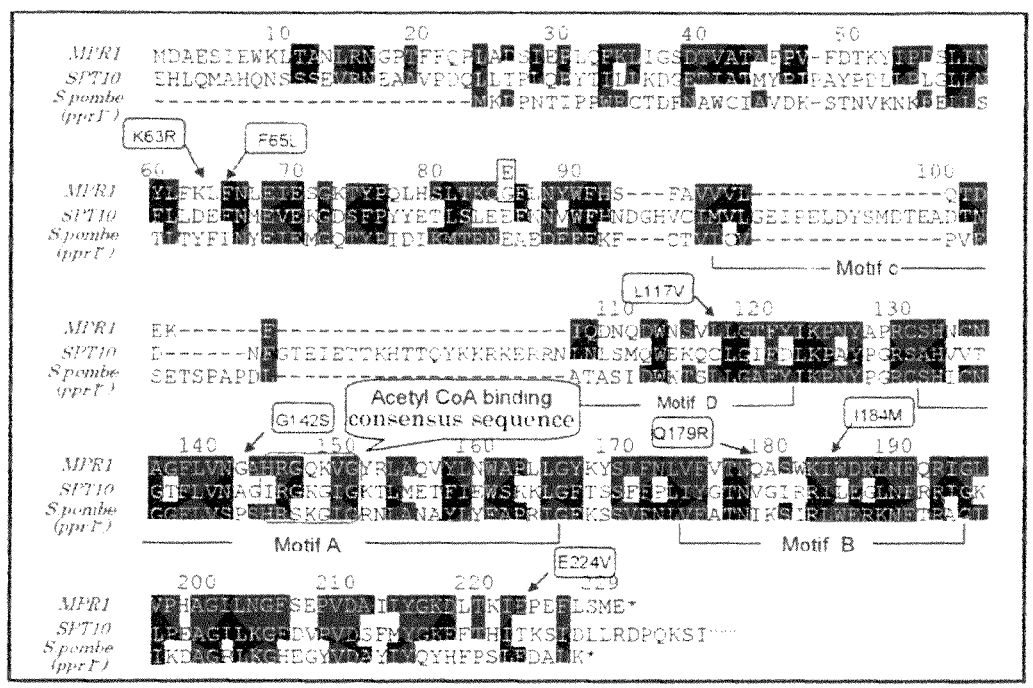
FIG. 5 shows a comparison of the primary structures of Mpr1 and other enzymes belonging to the acetyltransferase superfamily.
Figure 6A:
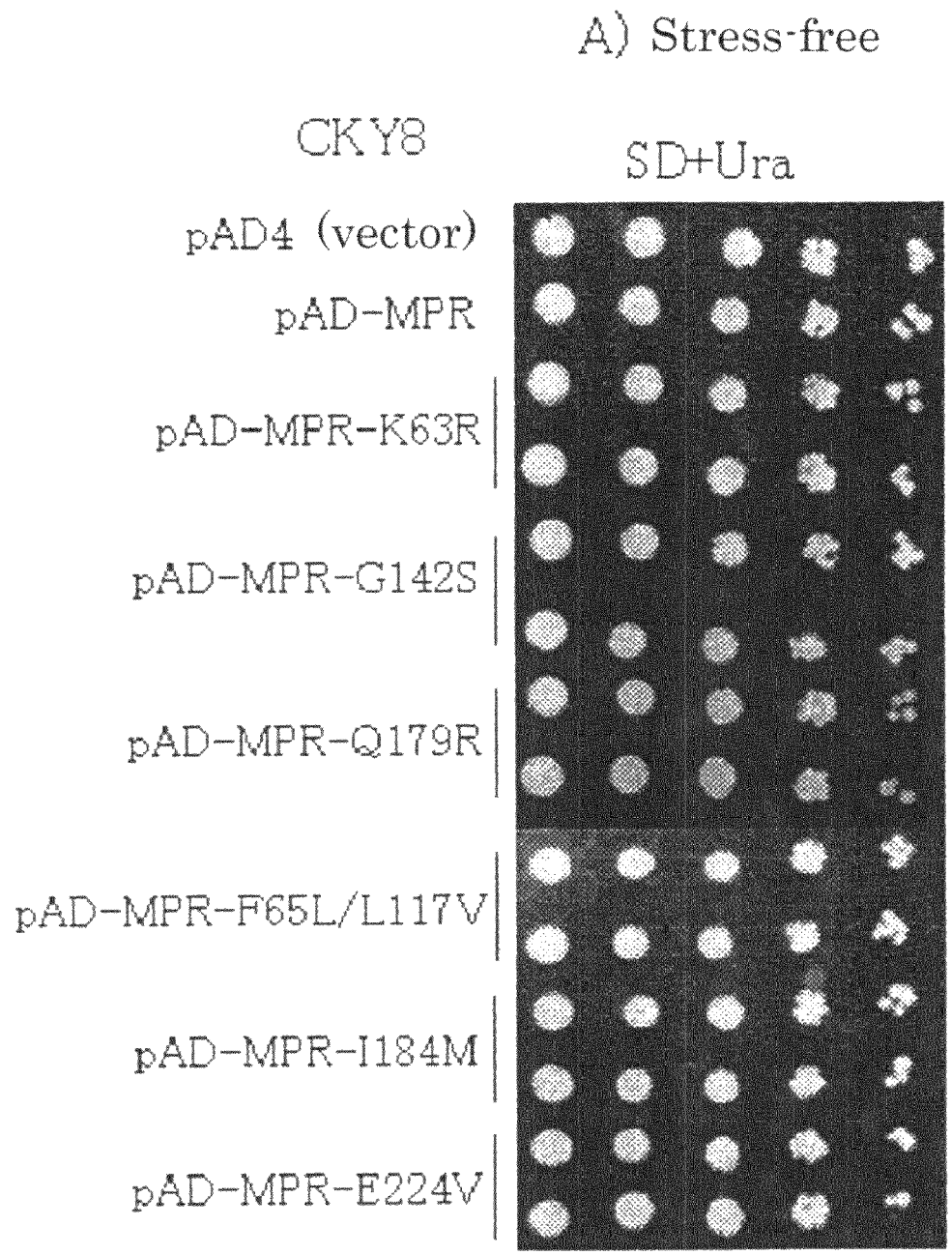
FIG. 6A shows the growth of the mutant-type MPR1 multicopy-introduced strains under the stress-free condition in the stress resistant test.
Figure 6B:
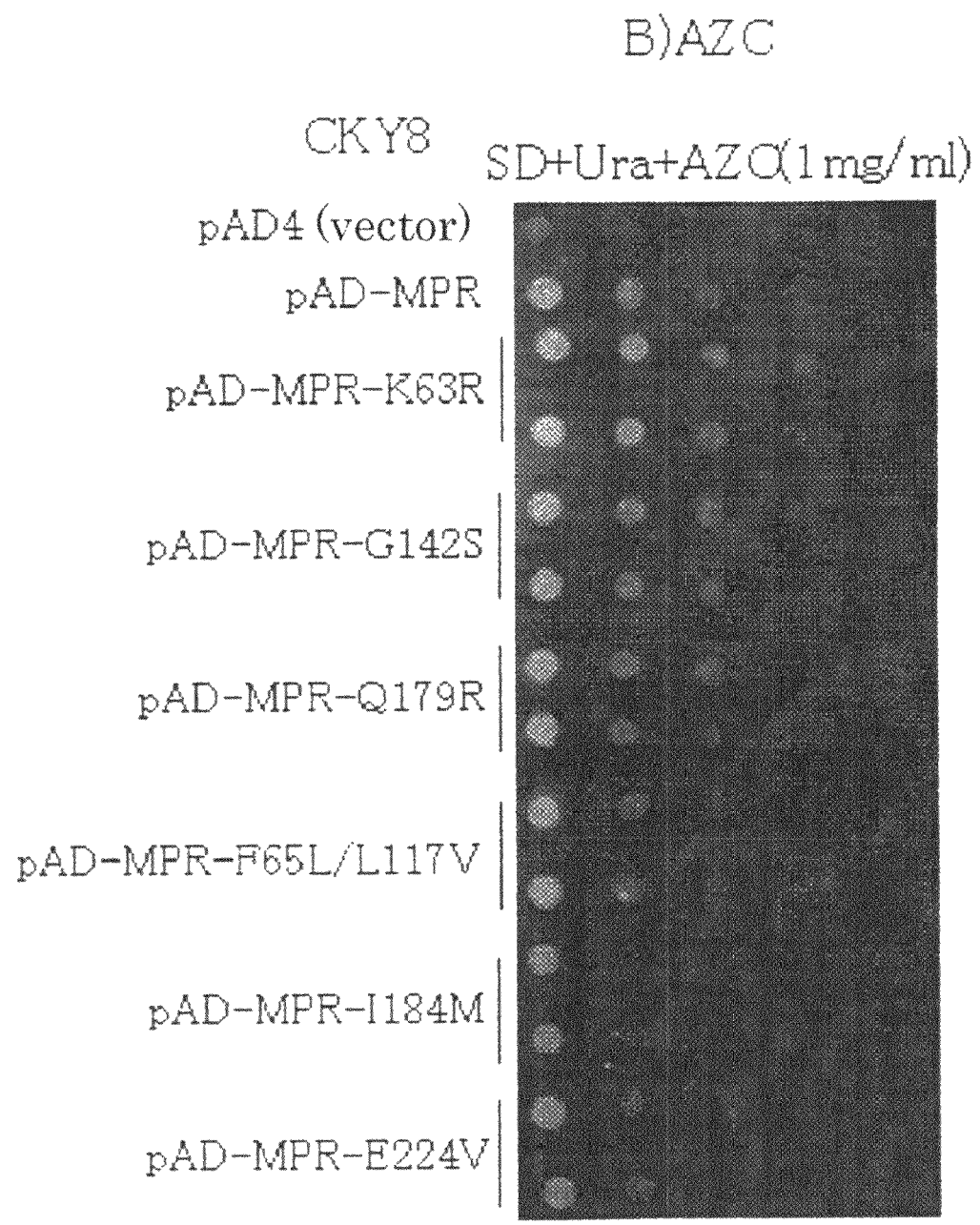
FIG. 6B shows the growth of the mutant-type MPR1 multicopy-introduced strains under the AZC stress condition in the stress resistant test.
Figure 6C:
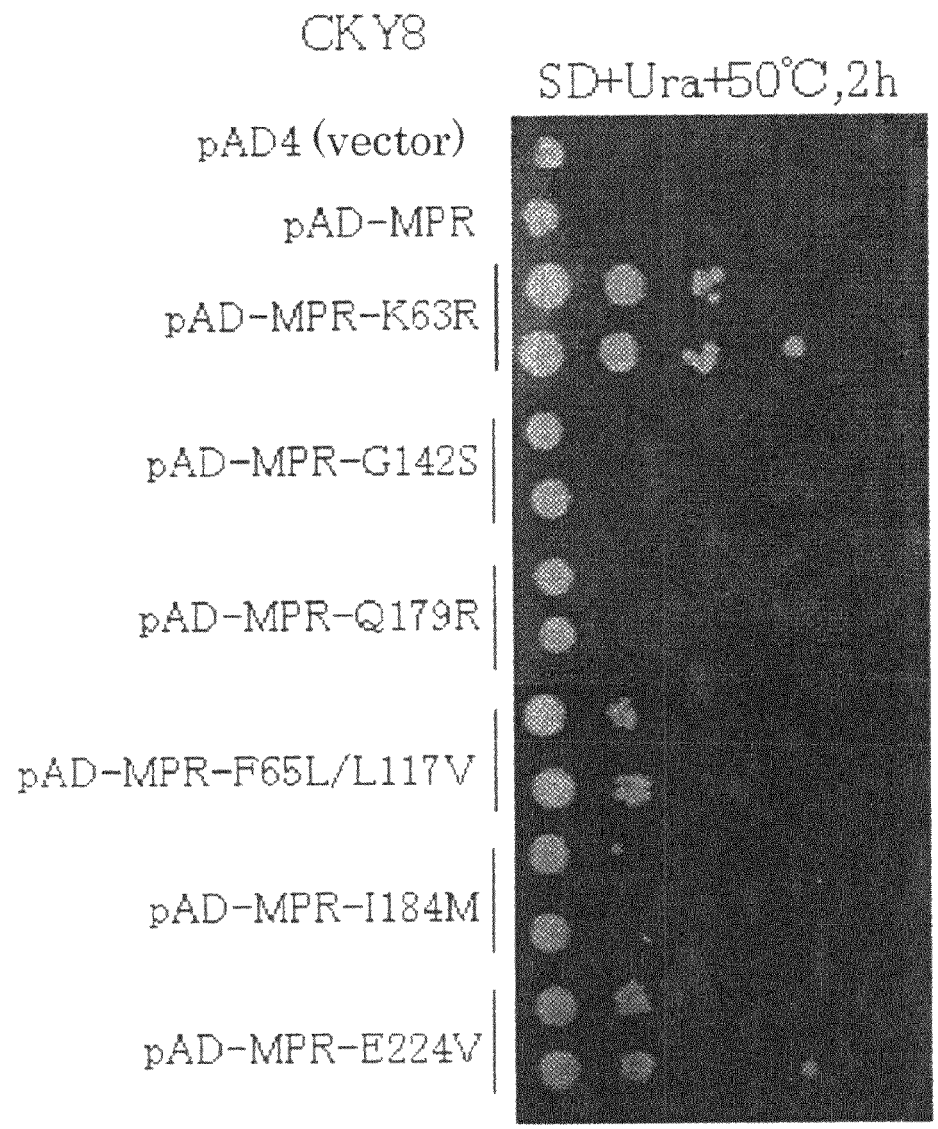
FIG. 6C shows the growth of the mutant-type MPR1 multicopy-introduced strains after being exposed to the heat shock stress in the stress resistant test.
Figure 6D:
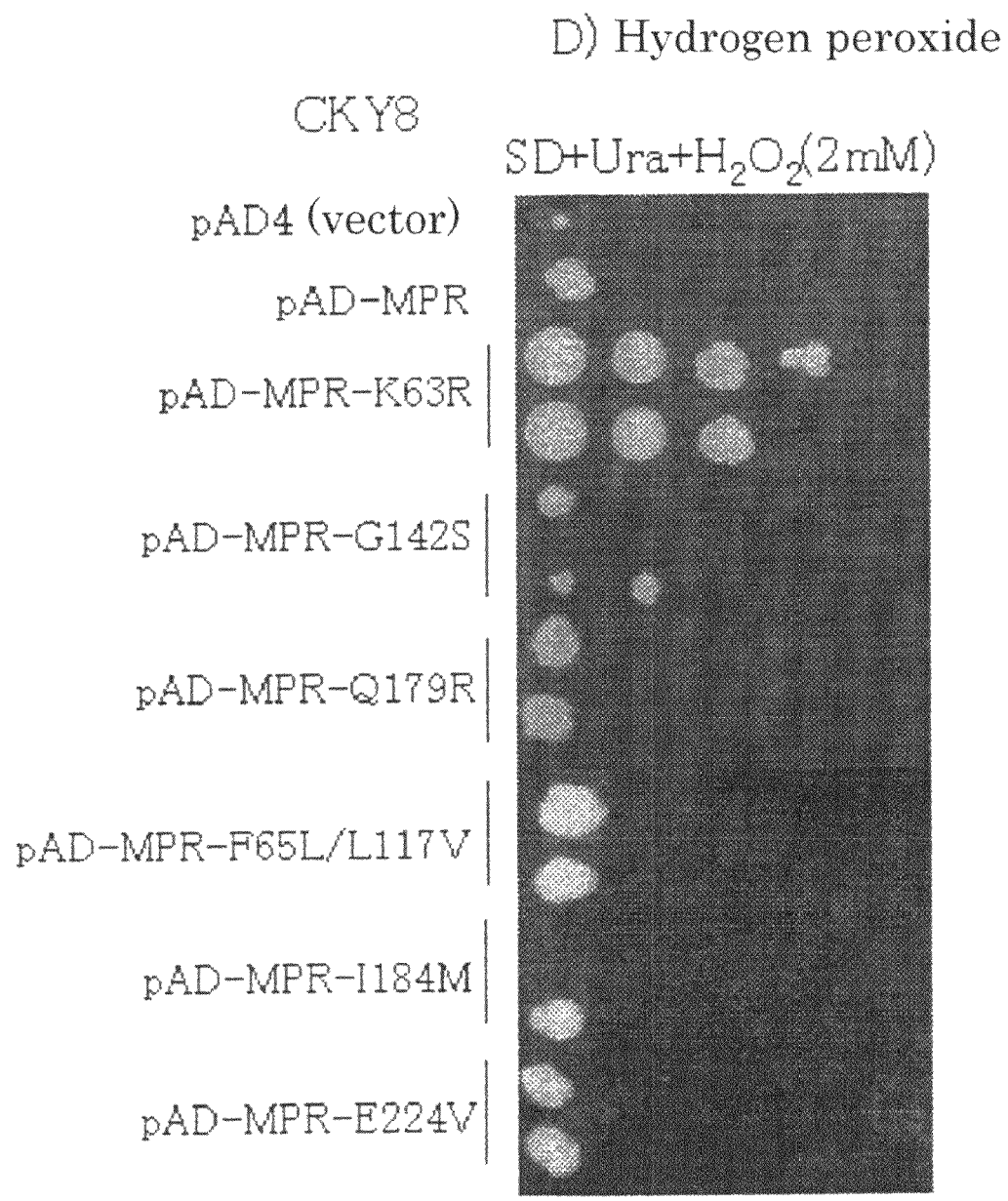
FIG. 6D shows the growth of the mutant-type MPR1 multicopy-introduced strains under the hydrogen peroxide stress in the stress resistant test.
Figure 7A:
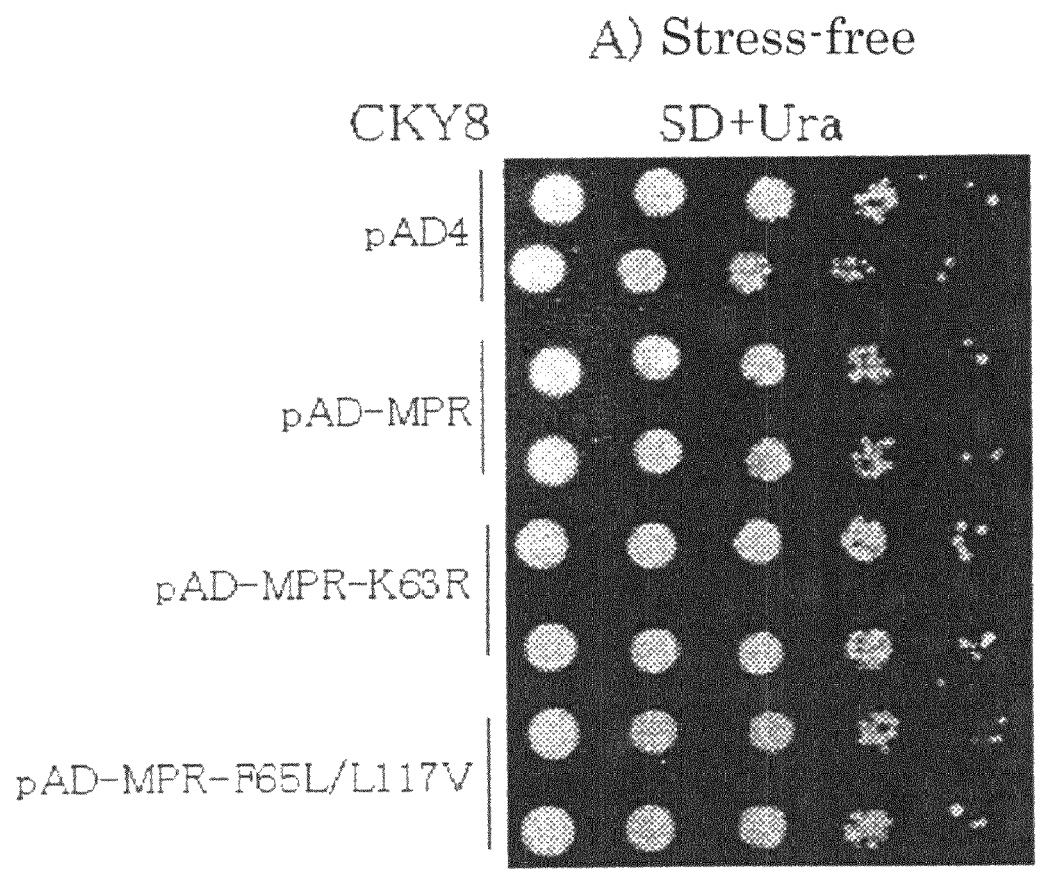
FIG. 7A shows the growth of the mutant-type MPR1 multicopy-introduced strains of the present invention under the stress-free condition in the stress resistant test.
Figure 7B:
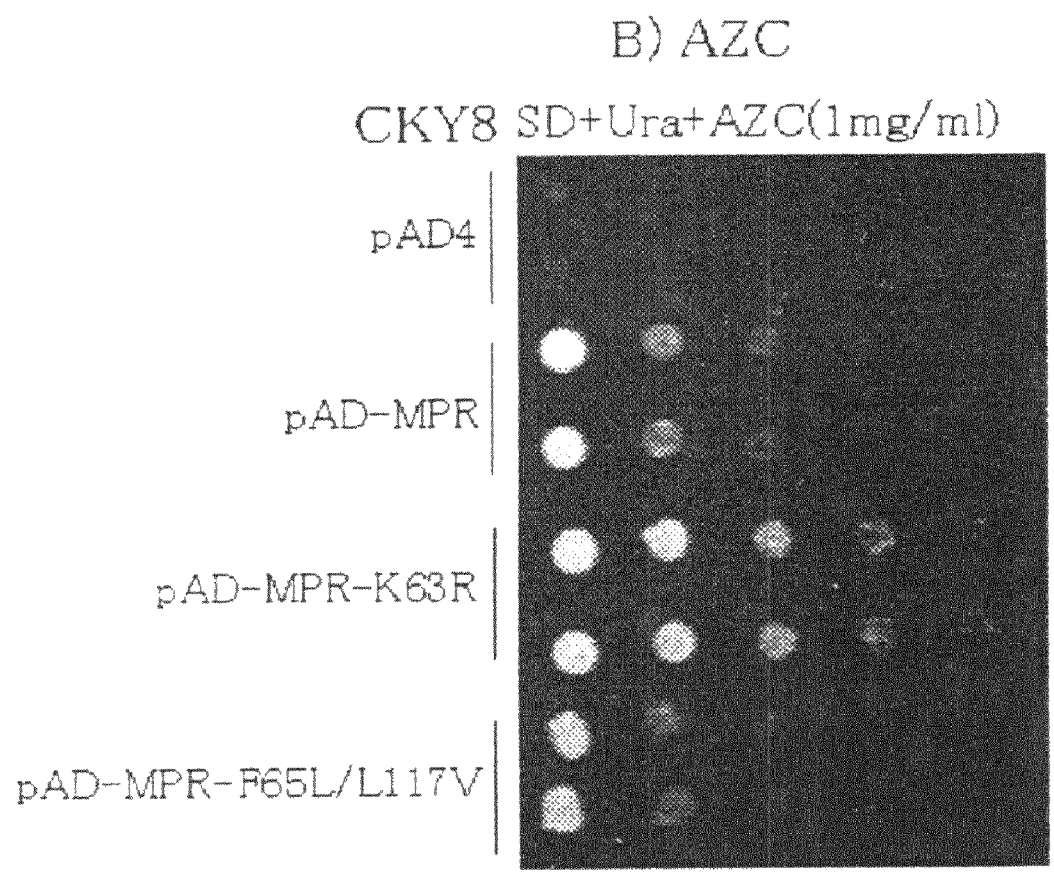
FIG. 7B shows the growth of the mutant-type MPR1 multicopy-introduced strains of the present invention under the AZC stress in the stress resistant test.
Figure 7C:
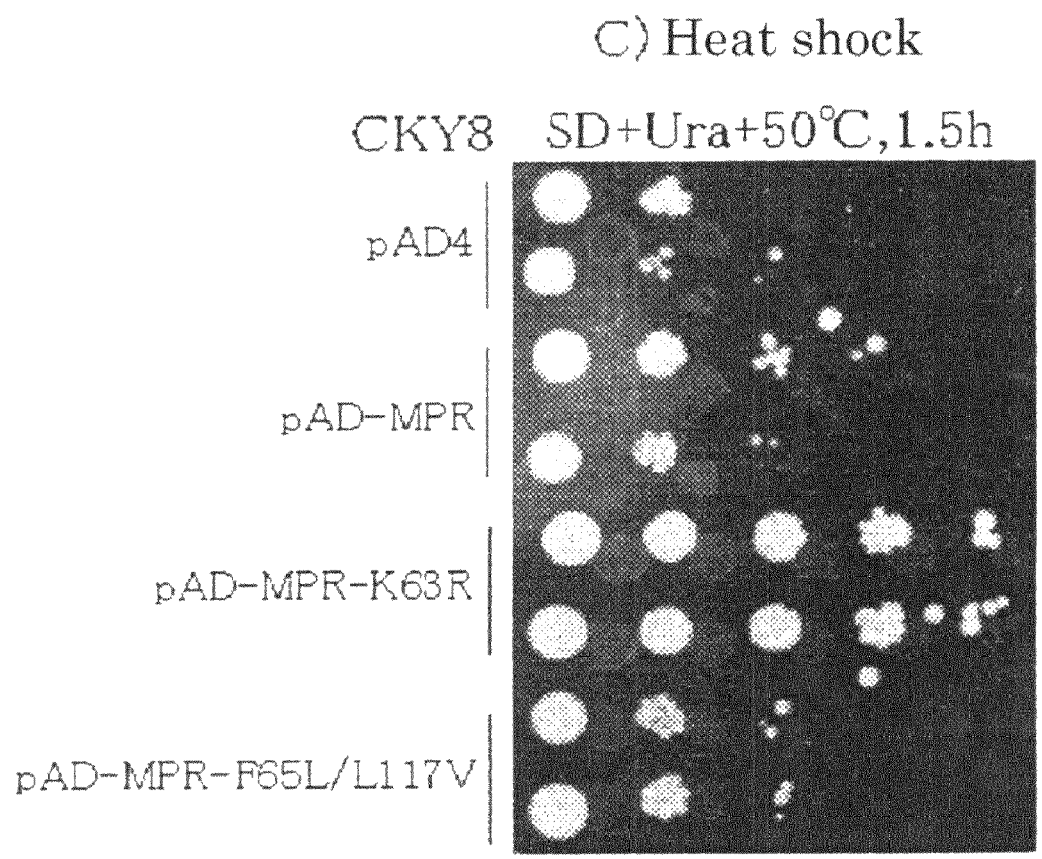
FIG. 7C shows the growth of the mutant-type MPR1 multicopy-introduced strains of the present invention after being exposed to the heat shock stress in the stress resistant test.
Figure 7D:
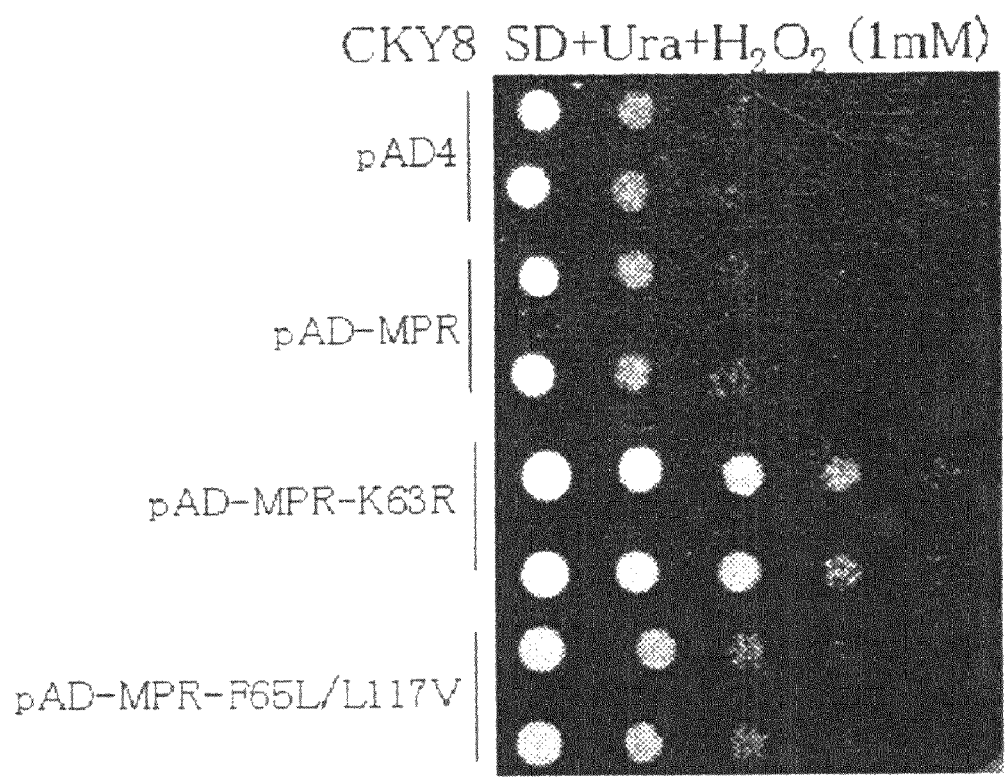
FIG. 7D shows the growth of the mutant-type MPR1 multicopy-introduced strain of the present invention under the hydrogen peroxide stress in the stress resistant test.
Figure 7E:
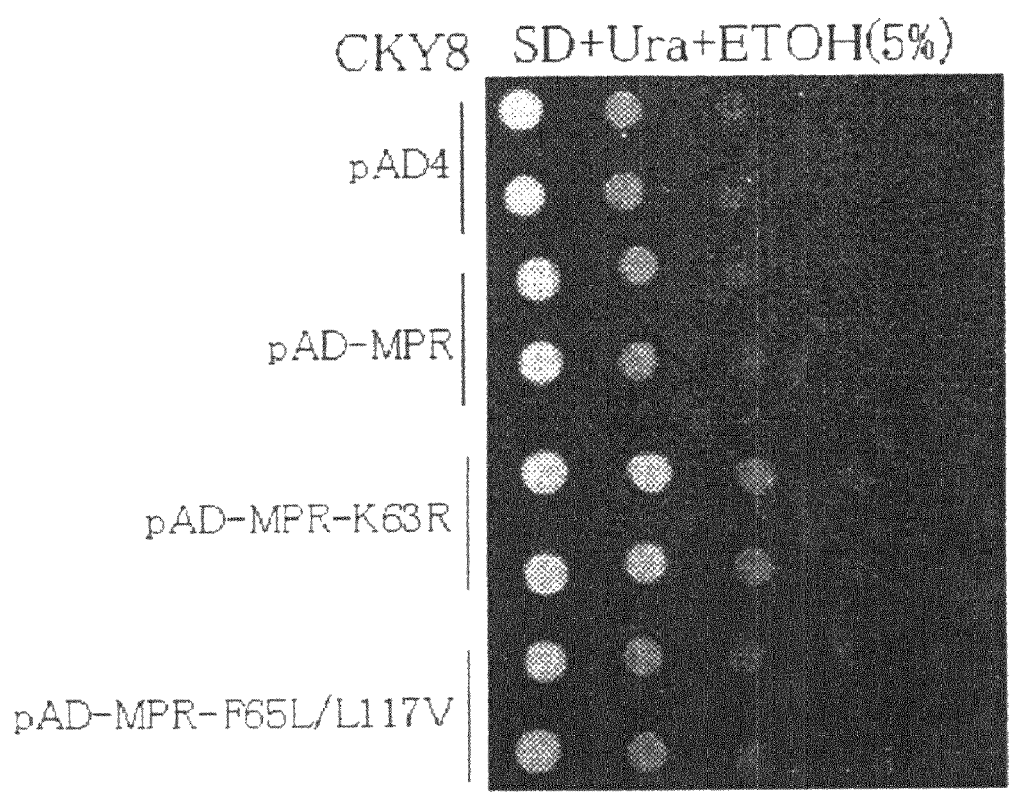
FIG. 7E shows the growth of the mutant-type MPR1 multicopy-introduced strains of the present invention under the ethanol stress in the stress resistant test.

The primary structures of the mutant-type Mpr1s obtained by the above-described screening and other acetyltransferases which show high homologies to the wild-type Mpr1 were compared and the mutational sites of the obtained mutant-type Mpr1s were confirmed. The result is shown in FIG. 5. G142S-Mpr1 is a substitution within motif A which comprises an acetyl-CoA binding consensus sequence. It was confirmed that Q179R, F65L/L117V and I184M-Mpr1s were also located within characteristic sequences which are conserved among the acetyltransferase superfamily.

Plasmids (the mutant-type pGAL-MPR) were extracted from the mutant-type Mpr1 clones obtained by the screening. In order to express MPR1 gene in pGAL-MPR, the expression must be induced by the medium whose carbon source is galactose. The growth rate in the medium comprising galactose is slow and the growth in the medium is unstable. In order to improve the efficiency of growth, the mutant-type pAD4-MPR1s were created by introducing the mutant-type MPR1s into pAD4 vector which allows gene expression in the presence of glucose. pAD4-MPR1-K63R and pAD4-MPR1-F65L/L117V were generated by amplifying ORFs of these mutant-type MPR1s by PCR using MPR-K63R and pGAL-MPR-G65L/L117V as templates and introducing the PCR products into HindIII-SacI site of pAD4. pAD4-MPR1-F65L and pAD4-MPR1-L117V were generated by amplifying the mutant-type gene fragments by site-directed mutagenesis PCR using pAD4-MPR as a template, treating the PCR products with HindIII and SacI restriction enzymes and introducing the PCR products into HindIII-SacI site of pAD4. CKY8 strains were transformed with the mutant-type pAD-MPR1s and were subjected to the stress sensitivity test. Firstly, the wild-type MPR1 multicopy-introduced strain, K63R-mutant-type MPR1-introduced strain and F65L/L117V-mutant-type Mpr1-introduced strain were cultured in SD+Ura medium until the cultures of the transformants reached the logarithmic growth phases. Then the culture media were serially diluted and the diluted media were spotted onto the medium.

The result is shown in FIG. 6. K63R-Mpr1-introduced strain which was obtained via the AZC stress screening system showed higher resistances to all of AZC (1 mg/ml), heat shock (2 hours) and hydrogen peroxide stress (2 mM) than the wild-type MPR1 multicopy-introduced strain (pAD-MPR1) which was used as a control. In particular, K63R-Mpr1-introduced strain showed a significantly high resistance to hydrogen peroxide stimulus (2 mM). F65L/L117V and E224V-Mpr1s which were obtained via the screening system comprising hydrogen peroxide stress-inducing medium did not show the improvement in resistances to AZC stress but did show the improved resistances to heat shock and hydrogen peroxide. Based on these results, K63R and F65L/L117V were chosen as the mutant-type acetyltransferase Mpr1s in order to further analyze the antioxidant capacity.

3) Analysis of Candidate Mutant-Type Mpr1s with Improved Functions (i) Spot Analysis of Mutant-Type Mpr1 Under the Oxidative Stress The stress resistances of K63R-mutant-type Mpr1 multicopy-introduced strain, F65L/L117V-mutant-type Mpr1 multicopy-introduced strain and the wild-type MPR1 multicopy-introduced strain were analyzed by the spot sensitivity test under the stress conditions of AZC (1 mg/ml), heat shock (50° C., 1.5 hours), hydrogen peroxide (1 mM) and ethanol (5%).

Strains used were CKY8 to which pAD4 was introduced (a negative control, MPR1•MPR2 non-carrying strain), CKY8 to which pAD-MPR was introduced (a control, MPR1-introduced strain) and CKY8 to which the mutant-type pAD-MPRs were introduced. Each strain was cultured in SD+Ura liquid medium until the culture reached the logarithmic growth phase and the culture was serially diluted. 2 μl of the diluted culture was spotted onto the each stress SD+Ura agar medium and cultured according to the protocol described in "Materials and Methods". Then the sensitivity (resistance) to each stress was determined.

The result is shown in FIG. 7. K63R mutant-type MPR1-introduced strain (pAD-MPR-K63R) which was obtained via the AZC stress-screening system showed significantly higher resistances to all the stresses (AZC, heat shock and hydrogen peroxide) compared to the wild-type MPR1. F65L/L117V mutant-type MPR1 (pAD-MPR-F65L/L117V) which was obtained via the hydrogen peroxide stress-screening system did not show any significant difference in the resistances to AZC, heat shock and ethanol stress compared to the wild-type MPR1. However, F65L/L117V mutant-type MPR1 (pAD-MPR-F65L/L117V) showed a higher resistance to hydrogen peroxide stress compared to the wild-type.

Figure 8:
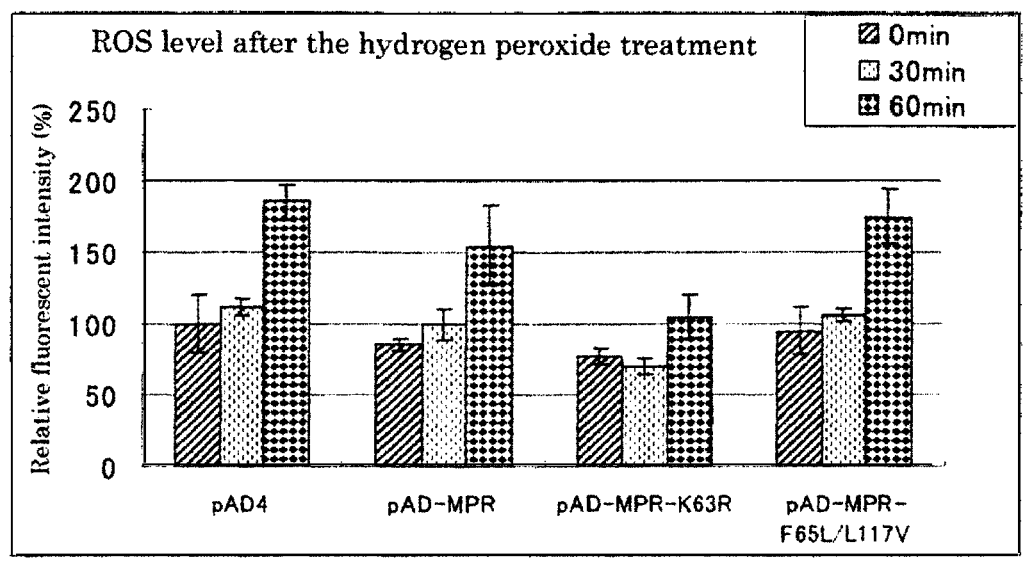
FIG. 8 shows the changes in the intracellular reactive oxygen species (ROS) level in yeasts after being exposed to the hydrogen peroxide treatment.

(ii) Comparison of the Survival Rate of Mutant-Type Mpr1 After $H_2O_2$ Treatment The survival rates of cells after the hydrogen peroxide treatment were examined. The cells used were CKY8 strain to which the wild-type MPR1 was introduced and CKY8 strain to which each of the mutant-type MPR1s (K63R, F65L/L117V, F65L and L117V-mutant-type Mpr1) was introduced. The experimental procedure was according to the description of "Materials and Methods". The cells to be tested were suspended in potassium phosphate buffer such that $OD_{600}$ of the suspension was 1.0 and the cells were treated with hydrogen peroxide at a final concentration of 3 mM (K63R, F65L/L117V) or 6 mM (F65L, L117V) for predetermined hours. Then, the suspension was applied onto YPD agar medium. The survival rates of the cells were calculated based on that the colony count at 0 hour after the hydrogen peroxide treatment is 100%. The result obtained by using 3 mM hydrogen peroxide treatment is shown in FIG. 8.

The decrease in the survival rate of the wild-type MPR1 multicopy-introduced strain (pAD-MPR) was smaller than those of MPR1 non-carrying strain (pAD4) until 2 hours after the hydrogen peroxide treatment. Further, the decreases in the survival rates of the mutant-type MPR1 multicopy-introduced strains (K63R, F65L/L117V-mutant-type Mpr1) were significantly smaller than those of the wild-type MPR1 multicopy-introduced strain (pAD-MPR). In particular, the decrease in the survival rate of K63R-Mpr1 was significantly smaller than that of the wild-type. Further, the survival rates of F65L and L117V-mutant-type Mpr1 multicopy-introduced strains were increased (data not shown).

(iii) Change in the Intracellular ROS Level of Mutant-Type Mpr1 after $H_2O_2$ Treatment The effects of the mutant-type Mpr1s and the wild-type Mpr1 carried by CKY8 on the increase in the ROS level after the hydrogen peroxide treatment were compared. The intracellular ROS level was measured by using $H_2$DCFDA which is a probe sensitive to intracellular oxides. $H_2$DCFDA can mainly detect hydrogen peroxide ($H_2O_2$), peroxyl radical (HOO·) and peroxyl nitrite anion ($ONOO^-$). Each strain was cultured until it reached the logarithmic growth phase and the cells were suspended in potassium phosphate buffer such that $OD_{600}$ of the suspension was 1.0. Thereafter, $H_2$DCFDA was added as described in "Materials and Methods" and the intracellular ROS level after the hydrogen peroxide treatment was measured.

Figure 9:
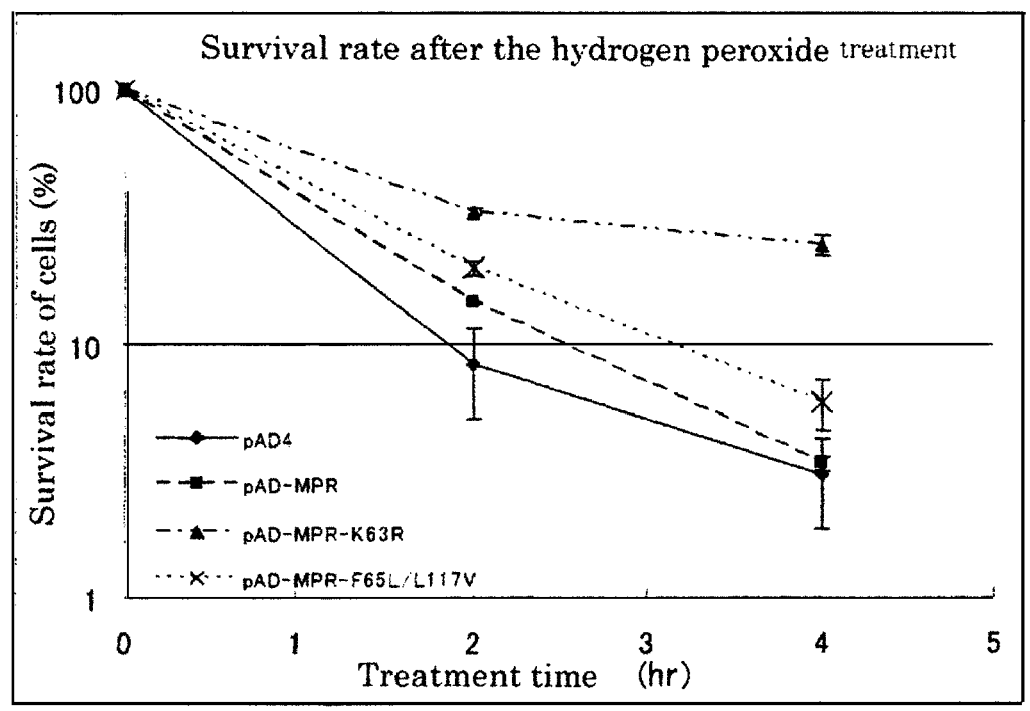
FIG. 9 shows the changes in the survival rate of the yeasts after being exposed to the hydrogen peroxide treatment. The longitudinal axis showing the survival rate is logarithmic.

The results of K63R and F65L/L117V-mutant-type Mpr1 multicopy-introduced strains are shown in Table 10 and FIG. 9. The increase in the intracellular ROS level after the hydrogen peroxide treatment of the wild-type MPR1 multicopy-introduced strain (pAD-MPR) was smaller than that of MPR1 non-carrying strain (pAD4). The increase in ROS level after 60 min treatment of K63R mutant-type Mpr1 with hydrogen peroxide was about 24% smaller than that of the wild-type MPR1 multicopy-introduced strain. Though the decrease in the survival rate of F65L/L117V mutant-type Mpr1 was smaller than that of the wild-type MPR1 multicopy-introduced strain, the ROS level of the F65L/L117V mutant-type Mpr1 was similar to that of MPR1 non-carrying strain. The ROS levels after 6 mM hydrogen peroxide treatment of F65L and L117V-mutant-type Mpr1 multicopy-introduced strains were examined. The intracellular ROS levels of the both strains were decreased (data not shown).

TABLE 10

| Plasmid | Relative fluorescence intensity (%) Hydrogen peroxide treatment hours (min) | | |
|---|---|---|---|
| | 0 min | 30 min | 60 min |
| pAD4 | 100 ± 20.3 | 1114 ± 5.5 | 185.1 ± 11.6 |
| pAD-MPR | 100 ± 5.2 | 115.4 ± 12.8 | 178.9 ± 31.8 |

TABLE 10-continued

| Plasmid | Relative fluorescence intensity (%) Hydrogen peroxide treatment hours (min) | | |
|---|---|---|---|
| | 0 min | 30 min | 60 min |
| pAD-MPR-K63R | 100 ± 6.9 | 91.8 ± 7.3 | 136.5 ± 19.5 |
| pAD-MPR-F65L/L117V | 100 ± 17.5 | 111.5 ± 4.6 | 185.9 ± 20.0 |

As described above, the strain to which K63R, F65L or L117V-mutant-type Mpr1 was introduced showed the decreased ROS level and the smaller decrease in the survival rate compared to the wild-type Mpr1-introduced strain. The strains to which mutant-type Mpr1s were introduced exhibited the improved oxidative stress resistance. It is believed that these strains improve the regulation efficacy of the ROS level under oxidative stress (hydrogen peroxide stress) and then lower the decrease in the survival rate. Further, the strain to which F65L/L117V mutant-type Mpr1 was introduced also exhibited the improved oxidative stress resistance.

The amino acid substitution positions (K63R and F65L) of the above two mutant-type enzymes are closely aligned on the primary structure and therefore, positions 63 to 65 of the amino acid sequence represented by SEQ ID NO: 1 are shown to be important for the antioxidant capacity of Mpr1.

4) Catalytic Activity and Stability of the Mutant-Type Enzyme

The wild-type enzyme and the mutant-type Mpr1 enzymes were purified and their catalytic activities when AZC and acetyl-CoA were used as substrates and their stabilities upon heat and hydrogen peroxide treatments were measured. The result is shown in Table 11, FIG. 10 and Table 12.

From the analysis of the kinetics (Table 11, changes are indicated by arrows), it is found that K63R mutant-type Mpr1 exhibited the decreased Km values for the both substrates, AZC and acetyl-CoA, and the catalytic activity of this mutant was improved. Further, F65L mutant-type Mpr1 exhibited the decreased Km value for AZC and the improved catalytic activity. Furthermore, L117V mutant-type Mpr1 exhibited the decreased Km value for acetyl-CoA and the improved catalytic activity. Additionally, F65L/L117V double-mutant-type Mpr1 exhibited the approximately same catalytic activity as the wild-type enzyme.

Figure 10:
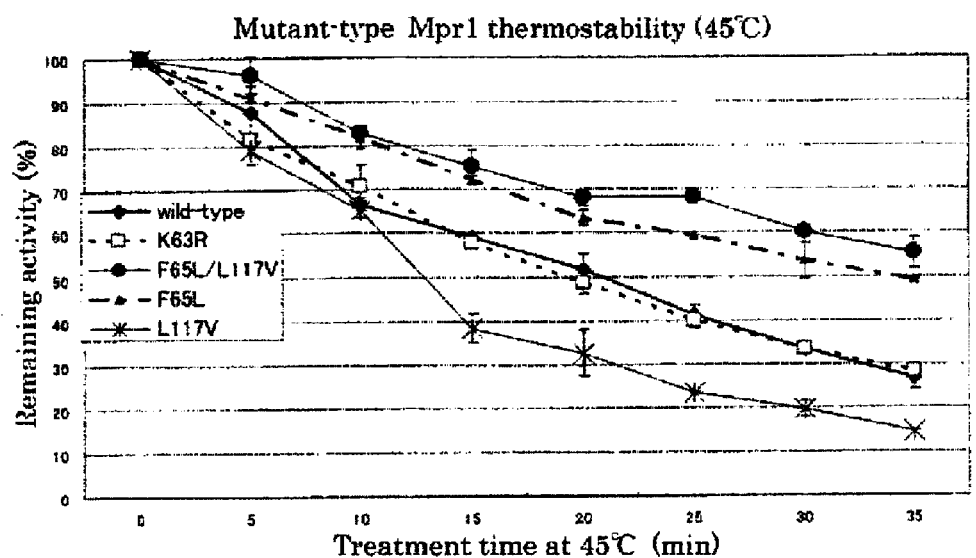
FIG. 10 shows the time course of the enzymatic activities of the mutant-type MPR1 enzymes of the present invention at a temperature of 45° C.

The thermal stabilities at 45° C. were measured (FIG. 10). As a result, F65L/L117V and F65L mutant-type Mpr1s showed the improved stabilities than the wild-type enzyme. K63R mutant-type Mpr1 showed the similar stability to the wild-type enzyme and L117V mutant-type Mpr1 showed the impaired stability than the wild-type enzyme.

Figure 11:
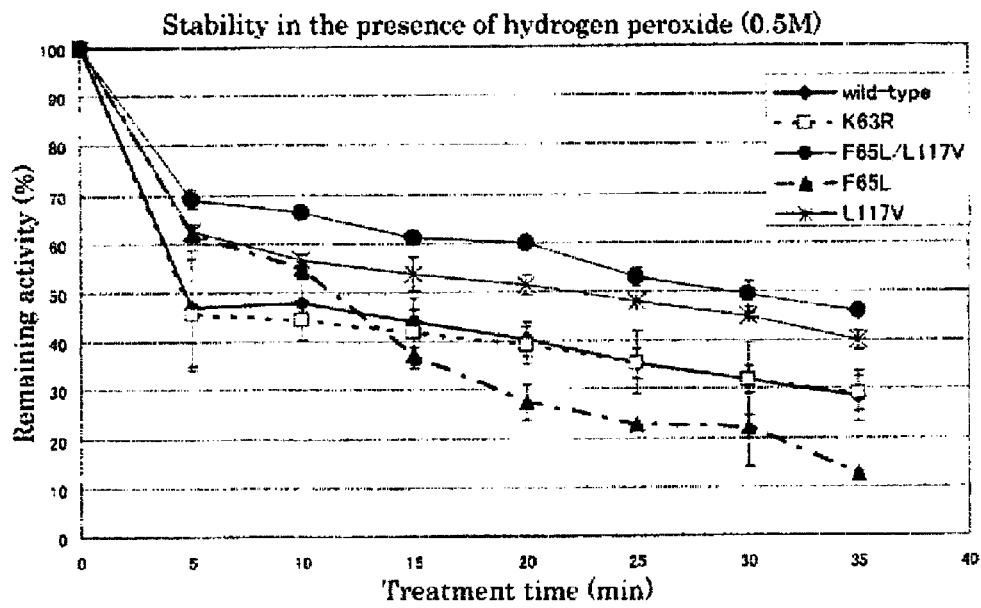
FIG. 11 shows the time course of the enzymatic activities of the mutant-type MPR1 enzymes of the present invention in the presence of hydrogen peroxide (0.5M).

The stabilities to hydrogen peroxide treatment were also measured (FIG. 11). As a result, F65L/L117V and L117V mutant-type Mpr1s showed the improved stabilities than the wild-type enzyme. K63R mutant-type Mpr1 showed the similar stability to the wild-type enzyme and F65L mutant-type Mpr1 showed the impaired stability than the wild-type enzyme.

TABLE 11

Mutant-type Mpr1 rate paramerter

| | AZC | | | | Acetyl-CoA | | | |
|---|---|---|---|---|---|---|---|---|
| | $K_m$(mM) | $k_{cat}(s^{-1})$ | $V_{max}$(U/mg) | $k_{cat}/K_m$ | $K_m$(μM) | $k_{cat}(s^{-1})$ | $V_{max}$(U/mg) | $k_{cat}/K_m$ |
| Wild-type | 1.6 ± 0.09 | 36.1 ± 1.53 | 74.76 ± 1.27 | 22.4 ± 1.25 | 12.6 ± 1.53 | 31.2 ± 0.63 | 64.5 ± 1.29 | 2.5 ± 0.26 |
| k63R | 1.2 ± 0.17 ↓ | 30.6 ± 1.44 | 72 ± 2.98 | 24.8 ± 2.55 | 8.0 ± 2.84 ↓ | 26.5 ± 0.94 | 62.4 ± 1.94 | 3.3 ± 1.09 ↑ |
| F65L/L117V | 1.8 ± 0.19 | 38.4 ± 2.18 | 79.4 ± 1.05 | 21.3 ± 1.61 | 13.3 ± 1.67 | 31.4 ± 0.17 | 64.9 ± 0.36 | 2.3 ± 0.32 |

TABLE 11-continued

| | Mutant-type Mpr1 rate paramerter | | | | | | | |
|---|---|---|---|---|---|---|---|---|
| | AZC | | | | Acetyl-CoA | | | |
| | $K_m$(mM) | kcat($s^{-1}$) | $V_{max}$(U/mg) | $k_{cat}/K_m$ | $K_m$(μM) | kcat($s^{-1}$) | $V_{max}$(U/mg) | $k_{cat}/K_m$ |
| F65L | 0.7 ± 0.15 ↓ | 31.4 ± 1.33 | 65.0 ± 2.74 | 45.5 ± 8.63 ↑ | 10.3 ± 1.46 | 30.8 ± 0.61 | 63.7 ± 3.34 | 2.9 ± 0.38 |
| L117V | 1.4 ± 0.13 | 47.6 ± 1.61 | 98.5 ± 3.34 | 32.5 ± 2.58 ↑ | 7.63 ± 2.03 ↓ | 38.4 ± 0.74 | 79.4 ± 1.54 | 5.0 ± 1.17 ↑ |

TABLE 12

| | Half-life of remaining activity: ½t (min) | |
|---|---|---|
| | Temp (45° C.) | $H_2O_2$ (0.5M) |
| Wild-type | 19.2 | 12.6 |
| K63R | 19.1 | 114 |
| F65L/L117V | 40.6↑ | 28.5↑ |
| F65L | 33.3↑ | 10.8↓ |
| L117V | 10.8↓ | 22.2↑ |

5) Proline-Accumulating-Wild-Type Mpr1-Introduced Yeast

Figure 12:
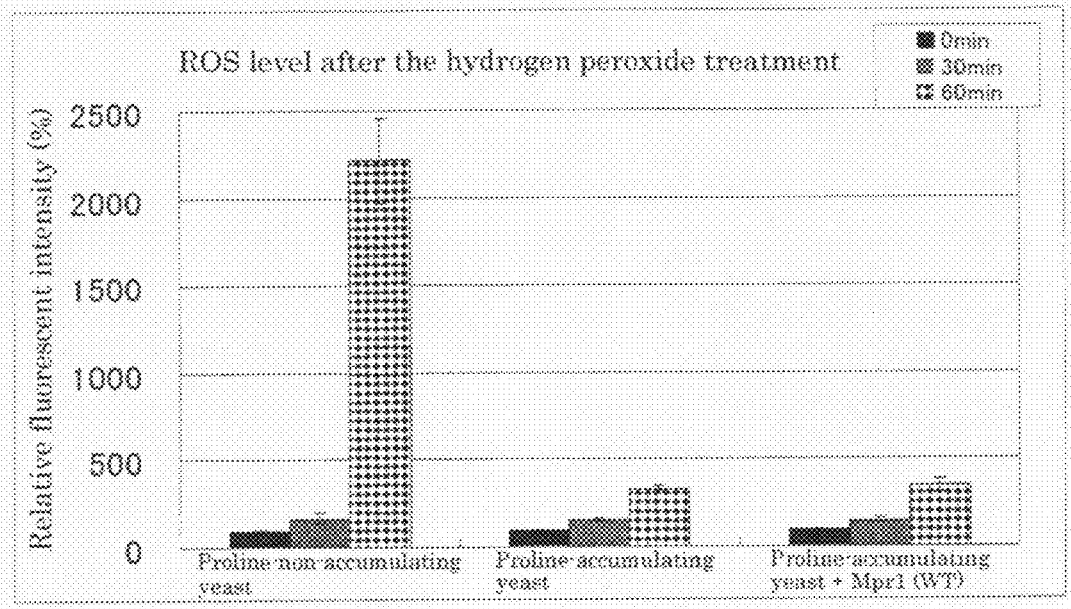
FIG. 12 shows the change in the intracellular ROS level after the hydrogen peroxide treatment of the proline accumulating yeasts to which the wild-type Mpr1 has been introduced.
Figure 13:
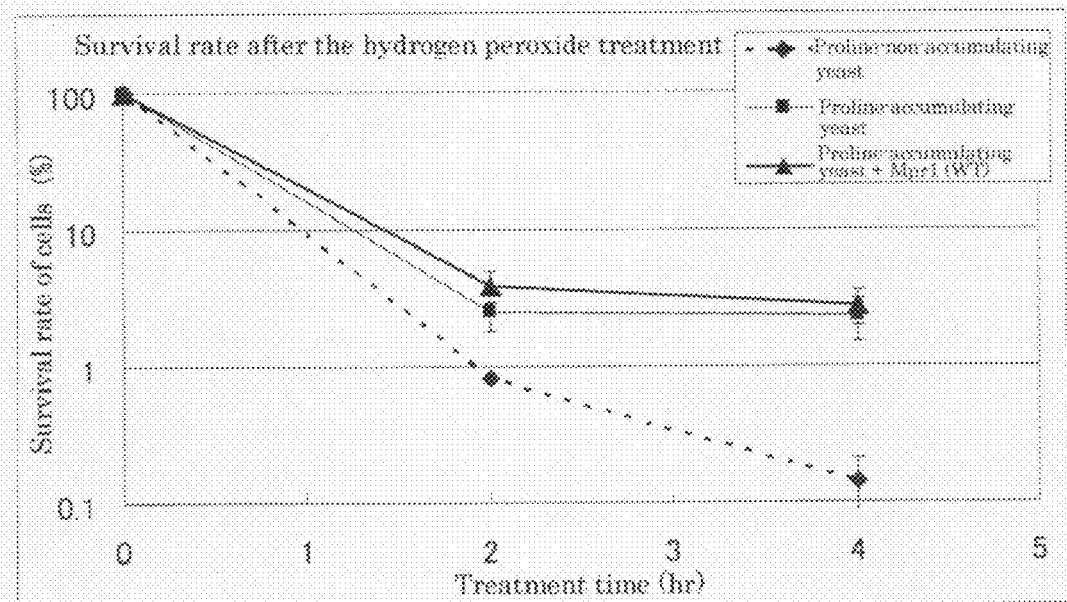
FIG. 13 shows the survival rates of the proline accumulating yeasts to which the wild-type Mpr1 has been introduced, after being exposed to the hydrogen peroxide treatment.

The changes in the intracellular ROS level and the survival rate under the condition of 6 mM hydrogen peroxide of the proline-accumulating yeast to which the wild-type Mpr1 was introduced were measured. The results are shown in FIGS. 12 and 13. The proline-accumulating yeast transformed with the wild-type Mpr1 did not show any significant differences in the ROS level and the survival rate compared to the proline-accumulating yeast.

6) Proline-Accumulating-Mutant-Type Mpr1-Introduced Yeast

Figure 14:
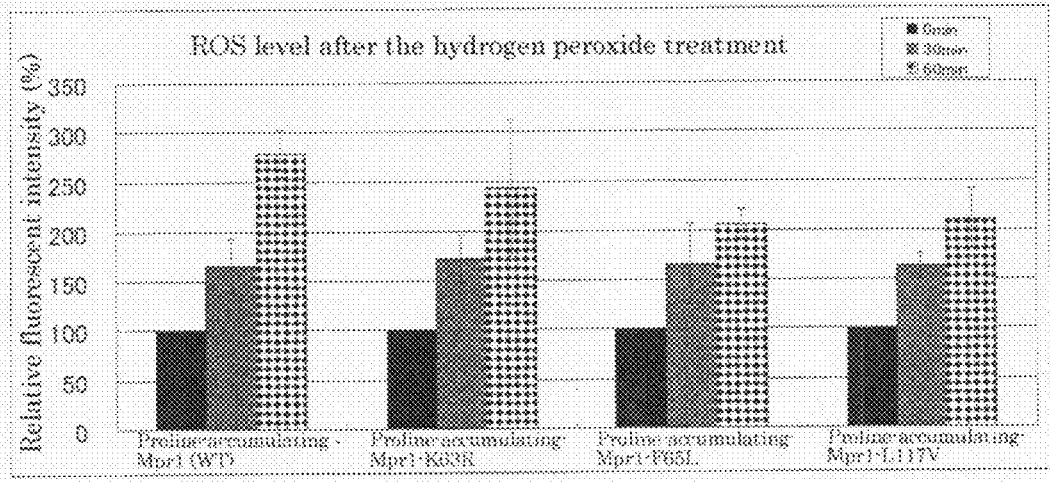
FIG. 14 shows the ROS level in the proline-accumulating yeasts to which the mutant-type Mpr1s of the present invention have been introduced, after being exposed to the hydrogen peroxide treatment.
Figure 15:
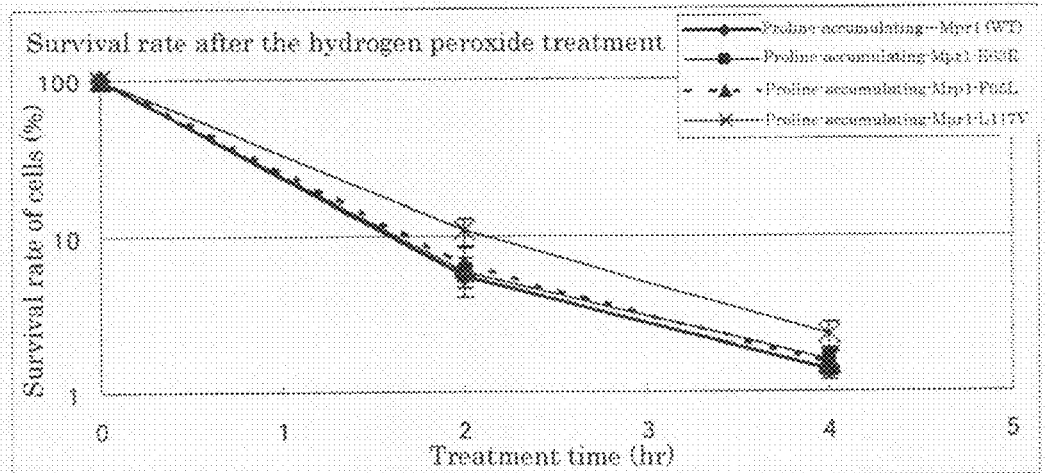
FIG. 15 shows the survival rates of the proline-accumulating yeasts to which the mutant-type Mpr1s of the present invention have been introduced, after being exposed to the hydrogen peroxide treatment.

The changes in the intracellular ROS level and the survival rate under the condition of 6 mM hydrogen peroxide of the proline-accumulating yeast to which mutant-type Mpr1s were introduced were measured. The results are shown in FIGS. 14 and 15. The proline-accumulating yeasts to which mutant-type Mpr1s were introduced exhibited the decreased intracellular ROS level than the proline-accumulating yeast to which the wild-type Mpr1 was introduced. In particular, the survival rate of the proline-accumulating yeast to which L117V mutant-type Mpr1 was introduced was significantly increased.

The invention claimed is:

1. A mutant-type acetyltransferase Mpr1: which comprises at least one amino acid substitution in the amino acid sequence of the wild-type Mpr1 of SEQ ID NO:1 which is selected from the group consisting of the Mpr1 whose Lys63 is substituted with Arg, Mpr1 whose Phe65 is substituted with Leu, Mpr1 whose Leu117 is substituted with Val and Mpr1 whose Phe65 and Leu117 are substituted with Leu and Val respectively, wherein said mutant-type acetyltransferase Mpr1 exhibits a higher antioxidant activity than that of the wild-type Mpr1.

2. An isolated nucleic acid which encodes the mutant-type acetyltransferase Mpr1 according to claim 1.

3. A recombinant vector comprising the isolated nucleic acid according to claim 2.

4. A transformed yeast comprising the isolated nucleic acid according to claim 2.

5. The transformed yeast according to claim 4, wherein said yeast is selected from the group consisting of laboratory yeast, baker's yeast, sake yeast, beer yeast, wine yeast and whiskey yeast.

6. The transformed yeast according to claim 4, wherein said yeast belongs to *Saccharomyces cerevisiae*.

7. The transformed yeast according to claim 6, wherein said yeast is a proline producing mutant-type yeast, which has a single amino acid replacement of Asp at position 154 by Asn in the wild-type gamma glutamate kinase.

8. The mutant-type acetyltransferase Mpr1 according to claim 1, which is selected from the group consisting of Mpr1 whose Lys63 is substituted with Arg and Mpr1 whose Phe65 and Leu117 are substituted with Leu and Val respectively.

* * * * *

SEQUENCE LISTING

```
<160> NUMBER OF SEQ ID NOS: 28

<210> SEQ ID NO 1
<211> LENGTH: 229
<212> TYPE: PRT
<213> ORGANISM: Saccharomyces cerevisiae

<400> SEQUENCE: 1

Met Asp Ala Glu Ser Ile Glu Trp Lys Leu Thr Ala Asn Leu Arg Asn
1               5                   10                  15

Gly Pro Thr Phe Phe Gln Pro Leu Ala Asp Ser Ile Glu Pro Leu Gln
            20                  25                  30

Phe Lys Leu Ile Gly Ser Asp Thr Val Ala Thr Ala Phe Pro Val Phe
        35                  40                  45

Asp Thr Lys Tyr Ile Pro Asp Ser Leu Ile Asn Tyr Leu Phe Lys Leu
    50                  55                  60

Phe Asn Leu Glu Ile Glu Ser Gly Lys Thr Tyr Pro Gln Leu His Ser
65                  70                  75                  80

Leu Thr Lys Gln Gly Phe Leu Asn Tyr Trp Phe His Ser Phe Ala Val
                85                  90                  95

Val Val Leu Gln Thr Asp Glu Lys Phe Ile Gln Asp Asn Gln Asp Trp
            100                 105                 110

Asn Ser Val Leu Leu Gly Thr Phe Tyr Ile Lys Pro Asn Tyr Ala Pro
        115                 120                 125

Arg Cys Ser His Asn Cys Asn Ala Gly Phe Leu Val Asn Gly Ala His
    130                 135                 140

Arg Gly Gln Lys Val Gly Tyr Arg Leu Ala Gln Val Tyr Leu Asn Trp
145                 150                 155                 160

Ala Pro Leu Leu Gly Tyr Lys Tyr Ser Ile Phe Asn Leu Val Phe Val
                165                 170                 175
```

```
Thr Asn Gln Ala Ser Trp Lys Ile Trp Asp Lys Leu Asn Phe Gln Arg
            180                 185                 190

Ile Gly Leu Val Pro His Ala Gly Ile Leu Asn Gly Phe Ser Glu Pro
            195                 200                 205

Val Asp Ala Ile Ile Tyr Gly Lys Asp Leu Thr Lys Ile Glu Pro Glu
210                 215                 220

Phe Leu Ser Met Glu
225

<210> SEQ ID NO 2
<211> LENGTH: 690
<212> TYPE: DNA
<213> ORGANISM: Saccharomyces cerevisiae

<400> SEQUENCE: 2
atggatgcgg aatccatcga atggaaacta actgcaaatt tacgtaatgg acctactttt      60
tttcaaccgt tagccgactc tattgaacca ttacagttca aacttatcgg atcggataca     120
gtggcaactg catttcctgt atttgacacc aaatatatac cggactcact cattaactat     180 cttttttaaat tgtttaattt ggaaattgaa agtggcaaga cttatccaca attgcacagt     240
ttgacaaaac agggattctt aaattattgg tttcattcat tcgctgtcgt tgttttgcaa     300
accgatgaga aatttattca agataatcaa gactggaatt cagttctctt gggcacattc     360
tacatcaagc ccaactatgc tccgcgttgc tcgcataatt gcaatgctgg ctttctagtt     420
aatggtgccc atagaggtca gaaggttggc tacaggcttg cccaggtata cttgaattgg     480
gcaccattgt tgggctataa atactctatc tttaatcttg tctttgttac caaccaagct     540
agttggaaaa tatgggacaa attaaacttt cagagaattg gactggtgcc tcatgccgga     600
attttgaatg gtttcagtga gcccgtggat gccattattt atggtaaaga tttgacaaaa     660
atagaacccg aattcctctc catggaataa                                      690

<210> SEQ ID NO 3
<211> LENGTH: 209
<212> TYPE: PRT
<213> ORGANISM: Schizosaccharomyces pombe

<400> SEQUENCE: 3

Met Lys Asp Pro Asn Thr Ile Pro Pro Trp Arg Cys Thr Asp Phe Asn
1                   5                   10                  15

Ala Trp Cys Ile Ala Val Asp Lys Ser Thr Asn Val Lys Asn Lys Glu
            20                  25                  30

Glu Leu Leu Ser Thr Leu Thr Tyr Phe Ile Asn Tyr Glu Ile Glu Met
        35                  40                  45

Gly Gln Thr Tyr Pro Ile Asp Ile Lys Met Thr Arg Asn Glu Ala Glu
    50                  55                  60

Asp Phe Phe Phe Lys Phe Cys Thr Val Ile Cys Val Pro Val Glu Ser
65                  70                  75                  80

Glu Thr Ser Pro Ala Pro Asp Leu Ala Thr Ala Ser Ile Asp Trp Lys
                85                  90                  95

Thr Ser Leu Leu Gly Ala Phe Tyr Ile Lys Pro Asn Tyr Pro Gly Arg
            100                 105                 110

Cys Ser His Ile Cys Asn Gly Gly Phe Leu Val Ser Pro Ser His Arg
        115                 120                 125

Ser Lys Gly Ile Gly Arg Asn Leu Ala Asn Ala Tyr Leu Tyr Phe Ala
    130                 135                 140
```

```
Pro Arg Ile Gly Phe Lys Ser Ser Val Phe Asn Leu Val Phe Ala Thr
145                 150                 155                 160

Asn Ile Lys Ser Ile Arg Leu Trp Glu Arg Leu Asn Phe Thr Arg Ala
                165                 170                 175

Gly Ile Ile Lys Asp Ala Gly Arg Leu Lys Gly His Glu Gly Tyr Val
            180                 185                 190

Asp Ala Tyr Ile Tyr Gln Tyr His Phe Pro Ser Leu Glu Asp Ala Leu
        195                 200                 205

Lys

<210> SEQ ID NO 4
<211> LENGTH: 630
<212> TYPE: DNA
<213> ORGANISM: Schizosaccharomyces pombe

<400> SEQUENCE: 4
atgaaggatc caaatactat tcctccatgg agatgtactg attttaatgc ttggtgcata    60
gccgttgata atctacaaa cgttaagaac aaagaagaat tactcagtac cttgacttat   120
ttcatcaact atgaaataga gatgggacag acttatccaa tcgacattaa atgactcgc   180 aatgaagcgg aagactttt ttttaaattt tgtactgtaa tctgtgttcc tgttgagagt   240
gagacatcac ctgctccaga tttggctacg gcttcaattg actggaaaac gagcttactc   300
ggtgccttct acattaagcc taactatccc ggtcgatgct ctcatatttg taatggtgga   360
ttttggtttt cacctagtca ccggagcaaa ggcattgggc gtaatttggc caatgcctat   420
ttgtactttg ctcctcgaat tggtttcaaa tcaagcgtgt taatctcgt tttcgctacc   480 aacataaaga gcattcgact atgggaaaga ctaaatttca cacgagccgg tattatcaaa   540
gatgctggta gacttaaggg tcatgaggga tacgtcgacg cttacatata ccaataccat   600
ttcccttcac ttgaagatgc cttaaaataa                                    630

<210> SEQ ID NO 5
<211> LENGTH: 231
<212> TYPE: PRT
<213> ORGANISM: Saccharomyces paradoxus

<400> SEQUENCE: 5

Met Asp Ala Glu Cys Ile Glu Trp Lys Ser Thr Ala Asn Leu His Asn
1               5                   10                  15

Gly Pro Ala Phe Phe Gln Pro Leu Thr Asp Ser Ile Glu Pro Leu Gln
            20                  25                  30

Phe Lys Leu Ile Gly Ser Asn Thr Leu Ala Thr Ala Phe Pro Val Phe
        35                  40                  45

Asp Thr Lys Tyr Ile Pro Asp Ser Leu Ile Asn Tyr Val Phe Ser Leu
    50                  55                  60

Phe Asn Met Glu Ile Glu Ser Gly Lys Thr Tyr Pro Gln Leu Asp Val
65                  70                  75                  80

Leu Thr Lys Gln Glu Phe Leu Lys Tyr Trp Phe His Ser Phe Ala Val
                85                  90                  95

Ile Val Leu Gln Thr Asp Lys Lys Tyr Ile Glu Asp Asn Gln Asp Trp
            100                 105                 110

His Ser Val Leu Leu Gly Thr Phe Tyr Ile Lys Pro Asn Tyr Ala Pro
        115                 120                 125

Arg Cys Ser His Asn Cys Asn Ala Gly Phe Leu Val Asn Ser Thr His
    130                 135                 140
```

```
Arg Gly Gln Lys Ile Gly Tyr Arg Leu Ala Gln Val Tyr Leu Asn Trp
145                 150                 155                 160

Ala Pro Leu Leu Gly Tyr Lys Tyr Ser Ile Phe Asn Leu Val Phe Val
                165                 170                 175

Thr Asn Lys Ala Ser Trp Lys Ile Trp Asp Arg Leu Asn Phe Gln Arg
            180                 185                 190

Ile Gly Leu Val Pro Cys Ala Gly Ile Leu Asn Asp Phe Ser Glu Pro
                195                 200                 205

Val Asp Ala Ile Ile Tyr Gly Lys Asp Leu Thr Lys Ile Glu Pro Glu
        210                 215                 220

Phe Leu Ser Met Glu Tyr Pro
225                 230

<210> SEQ ID NO 6
<211> LENGTH: 696
<212> TYPE: DNA
<213> ORGANISM: Saccharomyces paradoxus

<400> SEQUENCE: 6
atggatgcgg aatgcatcga atggaaatcg actgcaaatt tgcataatgg acctgctttt      60
ttccaaccgc taactgactc cattgaacca ttacagttca aacttattgg atcgaacaca     120
ctggcaaccg catttcctgt attcgacacc aaatatatac cggactcact tatcaactat     180
gttttagct tgttcaatat ggaaatcgaa agtggcaaaa cctatccaca attagatgtt      240
ttaactaagc aggaattctt aaaatattgg tttcactcat tcgccgttat tgttttgcaa     300
accgataaga aatatattga ggataatcaa gactggcatt cagttctctt aggtacattc     360
tacatcaagc ccaactatgc accgcgctgc tcccataatt gtaacgctgg gttttagtc     420
aatagtaccc atagaggtca gaagattggt tacaggcttg ctcaggtata cttgaattgg     480
gcacctttat tgggatataa atattctatc tttaatcttg tatttgttac caacaaagcc     540
agttggaaaa tatgggacag attaaacttc caaagaattg gattggtccc ttgtgctgga     600
attcttaatg atttagtga gcccgtggat gctataattt atggtaaaga cttgaccaaa     660
atagaacccg aattccttc catggaatac ccatag                                 696

<210> SEQ ID NO 7
<211> LENGTH: 229
<212> TYPE: PRT
<213> ORGANISM: Saccharomyces cerevisiae
<220> FEATURE:
<221> NAME/KEY: MUTAGEN
<222> LOCATION: (63)..(63)

<400> SEQUENCE: 7

Met Asp Ala Glu Ser Ile Glu Trp Lys Leu Thr Ala Asn Leu Arg Asn
1               5                   10                  15

Gly Pro Thr Phe Phe Gln Pro Leu Ala Asp Ser Ile Glu Pro Leu Gln
            20                  25                  30

Phe Lys Leu Ile Gly Ser Asp Thr Val Ala Thr Ala Phe Pro Val Phe
        35                  40                  45

Asp Thr Lys Tyr Ile Pro Asp Ser Leu Ile Asn Tyr Leu Phe Arg Leu
    50                  55                  60

Phe Asn Leu Glu Ile Glu Ser Gly Lys Thr Tyr Pro Gln Leu His Ser
65                  70                  75                  80
```

```
Leu Thr Lys Gln Gly Phe Leu Asn Tyr Trp Phe His Ser Phe Ala Val
                85                  90                  95

Val Val Leu Gln Thr Asp Glu Lys Phe Ile Gln Asp Asn Gln Asp Trp
            100                 105                 110

Asn Ser Val Leu Leu Gly Thr Phe Tyr Ile Lys Pro Asn Tyr Ala Pro
        115                 120                 125

Arg Cys Ser His Asn Cys Asn Ala Gly Phe Leu Val Asn Gly Ala His
    130                 135                 140

Arg Gly Gln Lys Val Gly Tyr Arg Leu Ala Gln Val Tyr Leu Asn Trp
145                 150                 155                 160

Ala Pro Leu Leu Gly Tyr Lys Tyr Ser Ile Phe Asn Leu Val Phe Val
                165                 170                 175

Thr Asn Gln Ala Ser Trp Lys Ile Trp Asp Lys Leu Asn Phe Gln Arg
            180                 185                 190

Ile Gly Leu Val Pro His Ala Gly Ile Leu Asn Gly Phe Ser Glu Pro
        195                 200                 205

Val Asp Ala Ile Ile Tyr Gly Lys Asp Leu Thr Lys Ile Glu Pro Glu
    210                 215                 220

Phe Leu Ser Met Glu
225

<210> SEQ ID NO 8
<211> LENGTH: 229
<212> TYPE: PRT
<213> ORGANISM: Saccharomyces cerevisiae
<220> FEATURE:
<221> NAME/KEY: MUTAGEN
<222> LOCATION: (65)..(65)

<400> SEQUENCE: 8

Met Asp Ala Glu Ser Ile Glu Trp Lys Leu Thr Ala Asn Leu Arg Asn
1               5                   10                  15

Gly Pro Thr Phe Phe Gln Pro Leu Ala Asp Ser Ile Glu Pro Leu Gln
            20                  25                  30

Phe Lys Leu Ile Gly Ser Asp Thr Val Ala Thr Ala Phe Pro Val Phe
        35                  40                  45

Asp Thr Lys Tyr Ile Pro Asp Ser Leu Ile Asn Tyr Leu Phe Lys Leu
    50                  55                  60

Leu Asn Leu Glu Ile Glu Ser Gly Lys Thr Tyr Pro Gln Leu His Ser
65                  70                  75                  80

Leu Thr Lys Gln Gly Phe Leu Asn Tyr Trp Phe His Ser Phe Ala Val
                85                  90                  95

Val Val Leu Gln Thr Asp Glu Lys Phe Ile Gln Asp Asn Gln Asp Trp
            100                 105                 110

Asn Ser Val Leu Leu Gly Thr Phe Tyr Ile Lys Pro Asn Tyr Ala Pro
        115                 120                 125

Arg Cys Ser His Asn Cys Asn Ala Gly Phe Leu Val Asn Gly Ala His
    130                 135                 140

Arg Gly Gln Lys Val Gly Tyr Arg Leu Ala Gln Val Tyr Leu Asn Trp
145                 150                 155                 160

Ala Pro Leu Leu Gly Tyr Lys Tyr Ser Ile Phe Asn Leu Val Phe Val
                165                 170                 175

Thr Asn Gln Ala Ser Trp Lys Ile Trp Asp Lys Leu Asn Phe Gln Arg
            180                 185                 190
```

```
Ile Gly Leu Val Pro His Ala Gly Ile Leu Asn Gly Phe Ser Glu Pro
        195                 200                 205

Val Asp Ala Ile Ile Tyr Gly Lys Asp Leu Thr Lys Ile Glu Pro Glu
    210                 215                 220

Phe Leu Ser Met Glu
225
```

<210> SEQ ID NO 9
<211> LENGTH: 229
<212> TYPE: PRT
<213> ORGANISM: Saccharomyces cerevisiae
<220> FEATURE:
<221> NAME/KEY: MUTAGEN
<222> LOCATION: (117)..(117)

<400> SEQUENCE: 9

```
Met Asp Ala Glu Ser Ile Glu Trp Lys Leu Thr Ala Asn Leu Arg Asn
1               5                   10                  15

Gly Pro Thr Phe Phe Gln Pro Leu Ala Asp Ser Ile Glu Pro Leu Gln
                20                  25                  30

Phe Lys Leu Ile Gly Ser Asp Thr Val Ala Thr Ala Phe Pro Val Phe
            35                  40                  45

Asp Thr Lys Tyr Ile Pro Asp Ser Leu Ile Asn Tyr Leu Phe Lys Leu
        50                  55                  60

Phe Asn Leu Glu Ile Glu Ser Gly Lys Thr Tyr Pro Gln Leu His Ser
65                  70                  75                  80

Leu Thr Lys Gln Gly Phe Leu Asn Tyr Trp Phe His Ser Phe Ala Val
                85                  90                  95

Val Val Leu Gln Thr Asp Glu Lys Phe Ile Gln Asp Asn Gln Asp Trp
            100                 105                 110

Asn Ser Val Leu Val Gly Thr Phe Tyr Ile Lys Pro Asn Tyr Ala Pro
        115                 120                 125

Arg Cys Ser His Asn Cys Asn Ala Gly Phe Leu Val Asn Gly Ala His
    130                 135                 140

Arg Gly Gln Lys Val Gly Tyr Arg Leu Ala Gln Val Tyr Leu Asn Trp
145                 150                 155                 160

Ala Pro Leu Leu Gly Tyr Lys Tyr Ser Ile Phe Asn Leu Val Phe Val
                165                 170                 175

Thr Asn Gln Ala Ser Trp Lys Ile Trp Asp Lys Leu Asn Phe Gln Arg
            180                 185                 190

Ile Gly Leu Val Pro His Ala Gly Ile Leu Asn Gly Phe Ser Glu Pro
        195                 200                 205

Val Asp Ala Ile Ile Tyr Gly Lys Asp Leu Thr Lys Ile Glu Pro Glu
    210                 215                 220

Phe Leu Ser Met Glu
225
```

<210> SEQ ID NO 10
<211> LENGTH: 229
<212> TYPE: PRT
<213> ORGANISM: Saccharomyces cerevisiae
<220> FEATURE:
<221> NAME/KEY: MUTAGEN
<222> LOCATION: (65)..(65)
<220> FEATURE:
<221> NAME/KEY: MUTAGEN
<222> LOCATION: (117)..(117)

-continued

<400> SEQUENCE: 10

```
Met Asp Ala Glu Ser Ile Glu Trp Lys Leu Thr Ala Asn Leu Arg Asn
1               5                   10                  15

Gly Pro Thr Phe Phe Gln Pro Leu Ala Asp Ser Ile Glu Pro Leu Gln
            20                  25                  30

Phe Lys Leu Ile Gly Ser Asp Thr Val Ala Thr Ala Phe Pro Val Phe
        35                  40                  45

Asp Thr Lys Tyr Ile Pro Asp Ser Leu Ile Asn Tyr Leu Phe Lys Leu
    50                  55                  60

Leu Asn Leu Glu Ile Glu Ser Gly Lys Thr Tyr Pro Gln Leu His Ser
65                  70                  75                  80

Leu Thr Lys Gln Gly Phe Leu Asn Tyr Trp Phe His Ser Phe Ala Val
                85                  90                  95

Val Val Leu Gln Thr Asp Glu Lys Phe Ile Gln Asp Asn Gln Asp Trp
            100                 105                 110

Asn Ser Val Leu Val Gly Thr Phe Tyr Ile Lys Pro Asn Tyr Ala Pro
        115                 120                 125

Arg Cys Ser His Asn Cys Asn Ala Gly Phe Leu Val Asn Gly Ala His
    130                 135                 140

Arg Gly Gln Lys Val Gly Tyr Arg Leu Ala Gln Val Tyr Leu Asn Trp
145                 150                 155                 160

Ala Pro Leu Leu Gly Tyr Lys Tyr Ser Ile Phe Asn Leu Val Phe Val
                165                 170                 175

Thr Asn Gln Ala Ser Trp Lys Ile Trp Asp Lys Leu Asn Phe Gln Arg
            180                 185                 190

Ile Gly Leu Val Pro His Ala Gly Ile Leu Asn Gly Phe Ser Glu Pro
        195                 200                 205

Val Asp Ala Ile Ile Tyr Gly Lys Asp Leu Thr Lys Ile Glu Pro Glu
    210                 215                 220

Phe Leu Ser Met Glu
225
```

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15
<211> LENGTH: 20
<212> TYPE: DNA
<213> ORGANISM: Artificial Sequence

```
<220> FEATURE:
<223> OTHER INFORMATION: Synthetic construct; 143(+)-9 primer

<400> SEQUENCE: 15
gctcgagaag cttcgaatgc                                               20

<210> SEQ ID NO 16
<211> LENGTH: 22
<212> TYPE: DNA
<213> ORGANISM: Artificial Sequence
<220> FEATURE:
<223> OTHER INFORMATION: Synthetic construct; 143(-)-4 primer

<400> SEQUENCE: 16
cgacgcgtcg ttattcgttc tt                                            22

<210> SEQ ID NO 17
<211> LENGTH: 45
<212> TYPE: DNA
<213> ORGANISM: Artificial Sequence
<220> FEATURE:
<223> OTHER INFORMATION: Synthetic construct; F65L(+) primer

<400> SEQUENCE: 17
attaactatc tttttaaatt gcttaatttg gaaattgaaa gtggc                   45

<210> SEQ ID NO 18
<211> LENGTH: 45
<212> TYPE: DNA
<213> ORGANISM: Artificial Sequence
<220> FEATURE:
<223> OTHER INFORMATION: Synthetic construct; F65L(-) primer

<400> SEQUENCE: 18
gccactttca atttccaaat taagcaattt aaaaagatag ttaat                   45

<210> SEQ ID NO 19
<211> LENGTH: 45
<212> TYPE: DNA
<213> ORGANISM: Artificial Sequence
<220> FEATURE:
<223> OTHER INFORMATION: Synthetic construct; L117V(+) primer

<400> SEQUENCE: 19
attaactatc tttttaaatt gcttaatttg gaaattgaaa gtggc                   45

<210> SEQ ID NO 20
<211> LENGTH: 39
<212> TYPE: DNA
<213> ORGANISM: Artificial Sequence
<220> FEATURE:
<223> OTHER INFORMATION: Synthetic construct; L117V(-) primer

<400> SEQUENCE: 20
cttgatgtag aatgtgccca ggagaactga attccagtc                          39

<210> SEQ ID NO 21
<211> LENGTH: 20
<212> TYPE: DNA
<213> ORGANISM: Artificial Sequence
<220> FEATURE:
<223> OTHER INFORMATION: Synthetic construct; pYES2(++) primer

<400> SEQUENCE: 21
gttacatgcg tacacgcgtc                                               20
```

<210> SEQ ID NO 22
<211> LENGTH: 21
<212> TYPE: DNA
<213> ORGANISM: Artificial Sequence
<220> FEATURE:
<223> OTHER INFORMATION: Synthetic construct; pYES2(-) primer

<400> SEQUENCE: 22
ggatcggact actagcagct g                                        21

<210> SEQ ID NO 23
<211> LENGTH: 20
<212> TYPE: DNA
<213> ORGANISM: Artificial Sequence
<220> FEATURE:
<223> OTHER INFORMATION: Synthetic construct; pAD4(++) primer

<400> SEQUENCE: 23
tcgtcattgt tctcgttccc                                          20

<210> SEQ ID NO 24
<211> LENGTH: 21
<212> TYPE: DNA
<213> ORGANISM: Artificial Sequence
<220> FEATURE:
<223> OTHER INFORMATION: Synthetic construct; pAD4(-) primer

<400> SEQUENCE: 24
gttttaaaac ctaagagtca c                                        21

<210> SEQ ID NO 25
<211> LENGTH: 26
<212> TYPE: DNA
<213> ORGANISM: Artificial Sequence
<220> FEATURE:
<223> OTHER INFORMATION: Synthetic construct; HindIII-MPR(+) primer

<400> SEQUENCE: 25
ggccaagctt agatggatgc ggaatc                                   26

<210> SEQ ID NO 26
<211> LENGTH: 30
<212> TYPE: DNA
<213> ORGANISM: Artificial Sequence
<220> FEATURE:
<223> OTHER INFORMATION: Synthetic construct; Sach-MPR(-) primer

<400> SEQUENCE: 26
ccccgagctc tgtctatgat tattccatgg                               30

<210> SEQ ID NO 27
<211> LENGTH: 1287
<212> TYPE: DNA
<213> ORGANISM: Saccharomyces cerevisiae
<220> FEATURE:
<221> NAME/KEY: CDS
<222> LOCATION: (1)..(1287)

<400> SEQUENCE: 27

```
atg aag gat gct aat gag agt aaa tcg tat act ata gtg atc aaa tta    48
Met Lys Asp Ala Asn Glu Ser Lys Ser Tyr Thr Ile Val Ile Lys Leu
1               5                   10                  15 ggc tct tca tcg cta gta gat gaa aaa acc aaa gaa cct aag tta gct    96
Gly Ser Ser Ser Leu Val Asp Glu Lys Thr Lys Glu Pro Lys Leu Ala
            20                  25                  30
```

```
                                                    -continued atc atg tcg ctt att gtc gaa act gta gtc aaa ttg aga aga atg gga       144
Ile Met Ser Leu Ile Val Glu Thr Val Val Lys Leu Arg Arg Met Gly
        35                  40                  45 cac aaa gtt atc atc gtg tcc agt ggt ggt att gct gtt ggt ttg agg       192
His Lys Val Ile Ile Val Ser Ser Gly Gly Ile Ala Val Gly Leu Arg
 50                  55                  60 act atg cgt atg aat aaa aga cca aaa cat tta gca gaa gtt cag gcc       240
Thr Met Arg Met Asn Lys Arg Pro Lys His Leu Ala Glu Val Gln Ala
 65                  70                  75                  80 atc gca gct att ggg cag ggt aga ttg atc ggg aga tgg gat ctt ctg       288
Ile Ala Ala Ile Gly Gln Gly Arg Leu Ile Gly Arg Trp Asp Leu Leu
                 85                  90                  95 ttt tcg caa ttt gat caa cgt atc gct caa att cta ttg acc aga aat       336
Phe Ser Gln Phe Asp Gln Arg Ile Ala Gln Ile Leu Leu Thr Arg Asn
            100                 105                 110 gat att ctg gac tgg acc caa tat aag aac gct caa aac aca att aat       384
Asp Ile Leu Asp Trp Thr Gln Tyr Lys Asn Ala Gln Asn Thr Ile Asn
        115                 120                 125 gaa ttg ttg aac atg ggc gtt att ccc att gtg aat gaa aac gac aca       432
Glu Leu Leu Asn Met Gly Val Ile Pro Ile Val Asn Glu Asn Asp Thr
    130                 135                 140 cta tct gtt aga gaa atc aaa ttt ggt gac aat gac act tta tca gca       480
Leu Ser Val Arg Glu Ile Lys Phe Gly Asp Asn Asp Thr Leu Ser Ala
145                 150                 155                 160 att act tct gct tta atc cat gca gat tat ctt ttc tta ctg aca gat       528
Ile Thr Ser Ala Leu Ile His Ala Asp Tyr Leu Phe Leu Leu Thr Asp
                165                 170                 175 gtt gac tgt ttg tat act gat aat cca agg aca aac cca gat gcc atg       576
Val Asp Cys Leu Tyr Thr Asp Asn Pro Arg Thr Asn Pro Asp Ala Met
            180                 185                 190 ccg atc tta gtt gtc cca gat ctc tca aag ggt ttg ccc ggt gtg aat       624
Pro Ile Leu Val Val Pro Asp Leu Ser Lys Gly Leu Pro Gly Val Asn
        195                 200                 205 act gct ggt ggt tca ggt tct gac gtt ggg acc ggt ggt atg gaa act       672
Thr Ala Gly Gly Ser Gly Ser Asp Val Gly Thr Gly Gly Met Glu Thr
    210                 215                 220 aaa ttg gtt gct gca gat ttg gca acg aat gcc ggt gtt cat acg ttg       720
Lys Leu Val Ala Ala Asp Leu Ala Thr Asn Ala Gly Val His Thr Leu
225                 230                 235                 240 atc atg aaa agc gat aca cct gcg aat ata ggt aga att gtc gag tat       768
Ile Met Lys Ser Asp Thr Pro Ala Asn Ile Gly Arg Ile Val Glu Tyr
                245                 250                 255 atg caa act cta gaa ctt gac gat gaa aat aaa gtt aaa caa gca tat       816
Met Gln Thr Leu Glu Leu Asp Asp Glu Asn Lys Val Lys Gln Ala Tyr
            260                 265                 270 aat ggc gat tta acg gat ttg caa aaa aga gaa ttt gag aaa tta aag       864
Asn Gly Asp Leu Thr Asp Leu Gln Lys Arg Glu Phe Glu Lys Leu Lys
        275                 280                 285 gct ctt aac gtt cca cta cat acg aag ttc att gct aat gat aat aaa       912
Ala Leu Asn Val Pro Leu His Thr Lys Phe Ile Ala Asn Asp Asn Lys
    290                 295                 300 cac cat cta aag aat aga gag ttt tgg att tta cac ggt ctt gtc tct       960
His His Leu Lys Asn Arg Glu Phe Trp Ile Leu His Gly Leu Val Ser
305                 310                 315                 320 aaa ggc gct gtt gtt ata gac caa ggt gcg tac cga gcc tta aca agg      1008
Lys Gly Ala Val Val Ile Asp Gln Gly Ala Tyr Arg Ala Leu Thr Arg
                325                 330                 335 aaa aat aag gcg gga tta ttg cca gca ggt gtt att gat gtt cag ggc      1056
Lys Asn Lys Ala Gly Leu Leu Pro Ala Gly Val Ile Asp Val Gln Gly
        340                 345                 350
```

```
act ttc cat gag tta gaa tgt gtt gac ata aaa gtt ggt aaa aag tta      1104
Thr Phe His Glu Leu Glu Cys Val Asp Ile Lys Val Gly Lys Lys Leu
            355                 360                 365 cca gat ggc acg tta gat cca gat ttt ccc ttg caa aca gta ggc aag      1152
Pro Asp Gly Thr Leu Asp Pro Asp Phe Pro Leu Gln Thr Val Gly Lys
    370                 375                 380 gca aga tgc aat tac acg agt tct gaa tta act aaa att aaa ggt ttg      1200
Ala Arg Cys Asn Tyr Thr Ser Ser Glu Leu Thr Lys Ile Lys Gly Leu
385                 390                 395                 400 cac agt gac caa atc gaa gag gaa ttg ggc tat aat gac agc gaa tat      1248
His Ser Asp Gln Ile Glu Glu Glu Leu Gly Tyr Asn Asp Ser Glu Tyr
                405                 410                 415 gtc gct cat aga gaa aat ttg gca ttc cca cct cgt tga                  1287
Val Ala His Arg Glu Asn Leu Ala Phe Pro Pro Arg
            420                 425

<210> SEQ ID NO 28
<211> LENGTH: 428
<212> TYPE: PRT
<213> ORGANISM: Saccharomyces cerevisiae

<400> SEQUENCE: 28

Met Lys Asp Ala Asn Glu Ser Lys Ser Tyr Thr Ile Val Ile Lys Leu
1               5                   10                  15

Gly Ser Ser Ser Leu Val Asp Glu Lys Thr Lys Glu Pro Lys Leu Ala
                20                  25                  30

Ile Met Ser Leu Ile Val Glu Thr Val Val Lys Leu Arg Arg Met Gly
            35                  40                  45

His Lys Val Ile Ile Val Ser Ser Gly Gly Ile Ala Val Gly Leu Arg
        50                  55                  60

Thr Met Arg Met Asn Lys Arg Pro Lys His Leu Ala Glu Val Gln Ala
65                  70                  75                  80

Ile Ala Ala Ile Gly Gln Gly Arg Leu Ile Gly Arg Trp Asp Leu Leu
                85                  90                  95

Phe Ser Gln Phe Asp Gln Arg Ile Ala Gln Ile Leu Leu Thr Arg Asn
            100                 105                 110

Asp Ile Leu Asp Trp Thr Gln Tyr Lys Asn Ala Gln Asn Thr Ile Asn
        115                 120                 125

Glu Leu Leu Asn Met Gly Val Ile Pro Ile Val Asn Glu Asn Asp Thr
130                 135                 140

Leu Ser Val Arg Glu Ile Lys Phe Gly Asp Asn Asp Thr Leu Ser Ala
145                 150                 155                 160

Ile Thr Ser Ala Leu Ile His Ala Asp Tyr Leu Phe Leu Leu Thr Asp
            165                 170                 175

Val Asp Cys Leu Tyr Thr Asp Asn Pro Arg Thr Asn Pro Asp Ala Met
        180                 185                 190

Pro Ile Leu Val Val Pro Asp Leu Ser Lys Gly Leu Pro Gly Val Asn
    195                 200                 205

Thr Ala Gly Gly Ser Gly Ser Asp Val Gly Thr Gly Gly Met Glu Thr
210                 215                 220

Lys Leu Val Ala Ala Asp Leu Ala Thr Asn Ala Gly Val His Thr Leu
225                 230                 235                 240

Ile Met Lys Ser Asp Thr Pro Ala Asn Ile Gly Arg Ile Val Glu Tyr
            245                 250                 255

Met Gln Thr Leu Glu Leu Asp Asp Glu Asn Lys Val Lys Gln Ala Tyr
        260                 265                 270
```

-continued

```
Asn Gly Asp Leu Thr Asp Leu Gln Lys Arg Glu Phe Glu Lys Leu Lys
        275                 280                 285

Ala Leu Asn Val Pro Leu His Thr Lys Phe Ile Ala Asn Asp Asn Lys
        290                 295                 300

His His Leu Lys Asn Arg Glu Phe Trp Ile Leu His Gly Leu Val Ser
305             310                 315                 320

Lys Gly Ala Val Val Ile Asp Gln Gly Ala Tyr Arg Ala Leu Thr Arg
                325                 330                 335

Lys Asn Lys Ala Gly Leu Leu Pro Ala Gly Val Ile Asp Val Gln Gly
            340                 345                 350

Thr Phe His Glu Leu Glu Cys Val Asp Ile Lys Val Gly Lys Lys Leu
        355                 360                 365

Pro Asp Gly Thr Leu Asp Pro Asp Phe Pro Leu Gln Thr Val Gly Lys
        370                 375                 380

Ala Arg Cys Asn Tyr Thr Ser Ser Glu Leu Thr Lys Ile Lys Gly Leu
385             390                 395                 400

His Ser Asp Gln Ile Glu Glu Glu Leu Gly Tyr Asn Asp Ser Glu Tyr
                405                 410                 415

Val Ala His Arg Glu Asn Leu Ala Phe Pro Pro Arg
            420                 425
```